(12) United States Patent
SenGupta et al.

(10) Patent No.: US 6,500,411 B2
(45) Date of Patent: Dec. 31, 2002

(54) MULTIFUNCTIONAL PARTICULATE ADDITIVE FOR PERSONAL CARE AND COSMETIC COMPOSITIONS, AND THE PROCESS OF MAKING THE SAME

(75) Inventors: Ashoke K. SenGupta, Barrington, IL (US); Ralph Spindler, Palatine, IL (US); Jerald W. Darlington, Jr., Marengo, IL (US)

(73) Assignee: Amcol International Corporation, Arlington Heights, IL (US)

( * ) Notice: Subject to any disclaimer, the term of this patent is extended or adjusted under 35 U.S.C. 154(b) by 0 days.

(21) Appl. No.: 10/068,268

(22) Filed: Feb. 5, 2002

(65) Prior Publication Data

US 2002/0182155 A1 Dec. 5, 2002

Related U.S. Application Data

(60) Provisional application No. 60/318,979, filed on Sep. 13, 2001, and provisional application No. 60/266,596, filed on Feb. 5, 2001.

(51) Int. Cl.[7] .............. A61K 7/00; A61K 7/42; A61K 7/44; A61K 31/74
(52) U.S. Cl. ............. 424/59; 424/401; 424/60; 424/78.02; 424/78.08; 424/400
(58) Field of Search ................ 424/400, 401, 424/59, 78.02, 78.08

(56) References Cited

U.S. PATENT DOCUMENTS

| | | |
|---|---|---|
| 5,207,998 A | 5/1993 | Robinson et al. ............. 424/59 |
| 5,512,276 A | 4/1996 | Lang et al. ............... 424/70.11 |
| 5,663,213 A | 9/1997 | Jones et al. ................. 523/105 |
| 5,721,306 A | 2/1998 | Tsipursky et al. ........... 524/449 |
| 5,952,095 A | 9/1999 | Beall et al. .................. 428/332 |
| 6,254,876 B1 | 7/2001 | de la Poterie et al. ...... 424/401 |
| 6,261,578 B1 | 7/2001 | Dupuis ........................ 424/401 |
| 2002/0054890 A1 | 5/2002 | Gers-Barlag et al. ........ 424/401 |

FOREIGN PATENT DOCUMENTS

| | | |
|---|---|---|
| DE | 44 15 087 A1 | 11/1995 |
| DE | 195 45 789 A1 | 6/1997 |
| DE | 29 51 319 A1 | 7/1998 |
| EP | 0 445 653 A1 | 9/1991 |
| EP | 0 530 084 B1 | 3/1993 |
| EP | 0 619 999 B1 | 10/1994 |
| EP | 0 659 403 B1 | 6/1995 |
| EP | 0 691 126 A1 | 1/1996 |
| EP | 0 824 086 A1 | 2/1998 |
| EP | 0 987 002 A2 | 3/2000 |
| EP | 0 022 017 A2 | 7/2000 |
| EP | 1 022 017 A2 | 7/2000 |
| JP | 60 115506 A | 6/1985 |
| JP | 0725988 A | 8/1995 |
| WO | WO 93 08230 | 4/1993 |
| WO | WO 99/20386 | 4/1999 |

OTHER PUBLICATIONS

Copy of Official International Search Report of European Patent Office in counterpart foreign application No. PCT/US02/03373 filed Feb. 5, 2002.

*Primary Examiner*—Shelley A. Dodson
(74) *Attorney, Agent, or Firm*—Marshall, Gerstein & Borun

(57) ABSTRACT

Cosmetic and personal care compositions can be manufactured using the multifunctional-additive compositions of the present invention. Such an additive preferably contains one or more particulate-based thickeners, such as a smectite clay, colloidal silica, laponite, and/or alumina, and most preferably one. or more smectite clays. According to one important embodiment of the present invention, the thickener particles are co-dispersed with particles of one or more particulate UVR-filters such as titanium dioxide, zinc oxide, or SUNSPHERE (available from International Specialty Chemicals, ISP), and most preferably with the natural particulate sunscreens such as the metal oxides. Another important component of the multifunctional-additive compositions is a dispersant or surface-modifier for the foregoing particulate materials, selected from the family of polyphenolic, natural polymers such as lignosulfonates, lignins, humates, tannates, and derivatives thereof. In addition, these compositions optionally include one or more of the following components: electrolytes, defoamers, humectants, emollients for cosmetics, preservatives, whiteners, and the like.

135 Claims, No Drawings

MULTIFUNCTIONAL PARTICULATE ADDITIVE FOR PERSONAL CARE AND COSMETIC COMPOSITIONS, AND THE PROCESS OF MAKING THE SAME

CROSS REFERENCE TO RELATED APPLICATIONS

This application claims the benefit under 35 U.S.C. §119 (e) of provisional applications Serial No. 60/266,596 filed Feb. 5, 2001, and Serial No. 60/318,979 filed Sep. 13, 2001.

FIELD OF THE INVENTION

The present invention relates to a multifunctional particulate additive for personal care and cosmetic formulations, and a process of making the same. More specifically, it relates to the following:

i) an additive composition that when added as a component in personal care and cosmetic formulations, can simultaneously serve one or more of the following purposes: i) improve the efficacy of sunscreen actives used as ultraviolet radiation (UVR) filters, ii) thicken hydrophilic solvents such as water, glycols, glycerine, and alcohols or mixtures of these solvents, iii) emulsify and stabilize oil droplets in oil-in-water (O/W) emulsions, and iv) function as an antioxidant;

ii) an additive that comprises a particulate-based thickener/gellant such as smectite clays and/or a particulate-based UV-filter such as titanium dioxide or zinc oxide, and certain types of dispersants or surface-modifiers for these particulate materials;

iii) natural polymer-based surface-modifiers that contain polarizable functional groups such as phenolic, catecholic, and other aromatic groups, as well as hydrogen bond-forming groups such as hydroxyl, phenol, carbonyl, and carboxyl groups, which in turn enable the adsorption of these macromolecules on a variety of particulate surfaces;

iv) natural polymer-based surface-modifiers of the type mentioned above, contained in the multifunctional additive, that can emulsify and stabilize oil droplets in an O/W emulsion, such that the polymer molecules act as an emulsifier/stabilizer when the multifunctional additive is used as a component in an O/W emulsion-based cosmetic formulation;

v) the use of the foregoing natural polymers as dispersants or surface-modifiers in order to increase the number-concentration of particles of the aforementioned particulate materials in a suspension, and/or to impart colloidal stability (stability against coagulation) of such suspended particles, which in turn promotes and/or preserves the thickening or UV-filtering ability of these particulate substances in cosmetic dispersions;

vi) an additive that can enhance the effectiveness of organic sunscreen-actives, and thus increase the sun protection factor (SPF), a measure of efficacy of UV-filters, of sunscreen products containing these UV-filters;

vii) the use of natural polymer-based surface-modifiers as components in the multifunctional additive, that are essentially polyphenols, by virtue of which the additive delivers antioxidant functionality;

viii) the use of surface-modifiers as components in the multifunctional additive, that are natural polymers, used in combination with natural thickeners, such as smectite clays, and natural particulate UV-filters, such as titanium dioxide and zinc oxide, catering to the consumer demand for the use of natural ingredients in cosmetics;

ix) a method of delivering various functional properties listed in section i), that are useful in personal care and cosmetic formulations, through a single additive and thus providing ease and cost-savings in product formulations;

x) an in-situ method for surface-modifying a particulate material such as smectite clays and thus producing the particulate in an aqueous gel, that allows the thickener functionality of the particulate to be realized in one or more hydrophilic solvents.

Examples of personal care and cosmetic products where the additive composition of the present invention may be used may include skin-care creams, lotions, facial creams, and sunscreens; hair care products such as shampoos, conditioners, colorants, and hair styling aids; liquid makeups, foundations, shaving creams and lotions. The additive can also be used in topical pharmaceutical formulations that can benefit from enhanced protection of the skin from harmful UV rays. The foregoing personal care, cosmetic, and pharmaceutical products can be in the form of oil-in-water emulsion or water-in-oil emulsion, or gel.

BACKGROUND OF THE INVENTION

I. Particulate-based Thickener

Smectite clays are a class of inorganic particulate materials that occur as stacks of individual, planar silicate layers referred to as platelets in the clay-literature. Examples of smectite clays include montmorillonite, bentonite, bidelite, hectorite, saponite, and stevensite.

These clays are popular particulate gellants or thickeners for aqueous compositions, particularly oil-in-water (O/W) emulsions. Fundamentally, the formation of particulate gels is a manifestation of suspended colloidal particles forming a network structure that entraps and thus immobilizes the suspending medium. Clay-based gels may form when individual platelets or stacks of a few aggregated platelets (tactoids) engage in interparticle associations with their neighboring platelets. If these particle-to-particle links extend throughout the total available volume, a gel, comprised of a continuous, linked particulate structure that entraps within itself the suspending medium, is formed. Such interparticle associations are governed by the interplay between the attractive and repulsive forces that generally act between particles suspended in a liquid. Hydrodynamic effects due to the orientation of planar clay particles in a flow-field may also contribute to the rheological properties of clay suspensions.

Clearly, the strength of particulate gels will depend on the number of interparticle associations in a given volume of the gel, implying that the greater the number-concentration of suspended particles, the stronger is the gel. Also, a dominance of the attractive interactions over the repulsive interactions, the likelihood of which increases with decrease in interparticle separation distance, is required for suspended particles to associate with their neighbors. An increase in the number-concentration of particles will tend to reduce their separation distances, an effect that could be especially dramatic for planar particles since the separation distance between two adjacent platelets will vary along their lengths when their faces do not align in parallel configuration. Nonetheless, too strong an attraction between adjacent clay platelets may draw them into strong association or coagulation, minimizing the particle number-concentration, once such coagulation occurs via face-to-face associations. In fact, it is these attractive forces that hold the clay platelets together in a stack.

Considering the above, the key to making clay-based gels is to ensure that there is sufficient interplatelet repulsion for the clay platelets to exfoliate (delaminate or deflocculate) under shear, releasing a large number of platelets as individual platelets or tactoids having fewer stacked platelets, that would then be available to form a particle network. On the other hand, in order to form a voluminous network structure, the net interaction (the sum of attractive and repulsive forces) between the delaminated platelets must be such that they can remain "bound" (attracted) to their neighboring platelets without being drawn into coagulation with their neighbors via face-to-face association. Accordingly, the gel-network may form if the delaminated platelets, while being separated from the surrounding platelets by as thick as possible an intervening layer of the suspending medium, reside in a relatively deep minimum in free energy of interaction with the neighboring platelets. Albeit physically separated from their neighbors, the individual platelets are no longer free to move independently, being trapped in a free energy minimum, producing in effect a continuous particle network, and hence thickening or gelation. Yet another way by which clay-based gels may form is where clay platelets coagulate due to edge-to-face associations, forming the so-called "card-house" structure described in clay literature.

Forming clay-based gels, as an outcome of the aforementioned phenomena, would require tuning of interplatelet forces, such as by modification of the clay-surface. Adding complexity, these attractive and repulsive forces may vary with the properties of the suspending medium. Evidence of this may be found in that the clay-based gels form far more easily in pure water than in hydrophilic organic solvents such as glycols, glycerols and alcohols.

It is therefore an object of the present invention to modify the surface of a particulate thickener/gellant, preferably a smectite clay, in a manner that provides for achieving the thickener-performance of the particulate material in water and/or in one or more hydrophillic solvents, particularly the solvents used in personal care and cosmetic product manufacturing. An underlying goal of such clay-surface modification is to stabilize the clay platelets against strong face-to-face aggregation, such that the suspended-state of the delaminated platelets may be preserved over extended time.

II. Particulate Sunscreens

Metal oxides such as titanium dioxide ($TiO_2$) and zinc oxide (ZnO) can serve as ultraviolet radiation (UVR) filters since they can scatter as well as absorb UVR. Clearly, the greater the number-concentration of particles available to scatter and/or absorb UVR, the higher will be the level of UV protection conferred by these particulate sunscreens. Therefore, a highly deflocculated state is required for the suspended metal oxide particles to perform most effectively as particulate UVR-filters. The use of dispersants (surface-modifiers) that could provide the suspended metal oxide particles with sufficient interparticle repulsion for effective deaggregation or deflocculation, could ensure such a finely-divided state of the particulate UVR-filter materials, and therefore a high level of UV protection.

An object of the present invention, therefore, is to produce a particulate-based additive for water-based and/or hydrophilic organic solvent-based cosmetic formulations, which contain one or more particulate UVR-filter materials in the form of highly deflocculated particles. Such a state of dispersion is attained and preserved by using dispersants (surface-modifiers), particularly, non-gum, non-starch, natural polymers, in order to meet the consumer demand for the use of natural ingredients in cosmetic products. Since the aforementioned additive may also contain one or more water-swellable, layered silicates as thickeners, in addition to one or more particulate UVR-filters, yet another object is to include those natural polymers in the additive, that can serve as dispersants both for layered silicate and particulate UVR-filter materials.

However, a strong dispersing effect of a dispersant on clay platelets may tend to oppose thickening or gelation in smectite clay dispersions. Therefore, a critical object of the present invention is to identify and use those natural polymers as dispersants or surface-modifiers that can deflocculate particles of UVR-filters effectively, while facilitating exfoliation of clay platelets and stabilizing the same against face-to-face coagulation, without strongly impeding thickening or gelation by the clay platelets. Polyphenolic compounds are known for their ability to serve as antioxidants, the functional ingredients that are highly desirable in the manufacturing of many cosmetic and personal care products. In order to ensure that the particulate-based additive disclosed herein provides for antioxidant functionality, an essential object of the present invention is to use those natural polymers as dispersants for the particulate components of the additive, which are polyphenols.

III. Emulsifier

A vast majority of cosmetic products are emulsions, mostly oil-in-water emulsions, and some water-in-oil emulsions. Emulsifiers are used to make these emulsions in a stable form such that the suspended oil droplets remain stable against flocculation and coalescence (fusion or aggregation of two or more droplets to form a bigger oil droplet) over extended time. The prior art teaches that even finely divided solid particles of latex, shale, clay, and other solid particles can stabilize emulsified oil droplets by adsorbing at the oil-water interface. Thickeners are added to emulsions for stabilizing emulsion droplets against sedimentation, a process known as creaming for O/W emulsions.

An additional object of the present invention is to use one or more natural polymer-based surface-modifiers for the particulate components of the disclosed multifunctional additive, wherein the surface-modifier can also serve as an emulsifier in personal care and cosmetic compositions. Conceivably, once surface-modified by such a polymer, the particulate components of the additive, such as smectite clays and/or the metal oxide-based UVR filters, may be rendered in a form where they may actually contribute towards emulsion-stabilization by adsorbing as colloidal solids at the oil-water interface.

IV. Organic Sunscreens

Ultraviolet radiation-absorbing organics, such as octyl methoxycinamate, homosalate, octocrylene, octyl salicylate, oxybenzone, methybenzylidene camphor, phenylbenzimaidazole sulfonic acid, ethylhexyl triazone, methyl anthranilate, and avobenzone are oil-like substances that are generally emulsified into cosmetic compositions to deliver UVR protection functionality. European patent application EP 0 619 999 reveals that a synergy in SPF can be found when particulate inorganic oxides such as titanium dioxide, zinc oxide, and iron oxide are used in combination with an organic sunscreen. In EP 0 619 999, the average primary (single or completely deflocculated) particle size for the inorganic particulates is less than 0.2 micron. Also, according to a preferred embodiment, the oxide particulates are incorporated in cosmetic compositions containing an organic sunscreen, in the form of an aqueous dispersion prepared by milling the inorganic oxide in the presence of a dispersant such as a polyacrylate or derivatives thereof.

Nonetheless, during the course of the present invention, it was found that increased SPF of organic sunscreen formulations could not be achieved in every case, even though the formulations contained particulate materials including titanium dioxide ($TiO_2$) at relatively high concentrations. Given, however, that the $TiO_2$ material used was a pigment-grade material with an average primary particle size of 0.3 micron and a maximum particle size of 1 micron, rather than the particulate $TiO_2$ prescribed in EP 0 619 999, with an average primary particle size of less than 0.2 micron. Obtaining particulate materials such as inorganic oxides and silicates with an average primary particle size of less than 0.1–0.2 micron will require expensive milling or separation techniques. It is, therefore, an object of the present invention to be able to produce a particulate-based additive for cosmetic and personal care products, which can enhance the SPF of organic sunscreens, even when the average primary particle size for the particulate components of the additive is larger than 0.2 micron. In such an additive, the particulate components, preferably, do not just include an inorganic oxide including the inorganic UVR-filters, but also a smectite clay such that the additive may provide for thickening or gelation of hydrophilic solvents used in the manufacturing of cosmetic and personal care products. Also, as indicated earlier, an essential object of the present invention is that the particulate components of the multifunctional additive disclosed herein would have to be surface-modified necessarily with a natural polymer, and to achieve the full advantage of the present invention, with a polyphenolic natural polymer, such that the additive may provide for antioxidant functionality. While some natural polymers (carboxymethyl cellulose and xanthan gum) are disclosed in EP 0 619 999, these natural polymers do not present any molecular or structural features or components (for example, phenolic groups) that would allow them to function as an antioxidant. Also, these polymers are generally not very effective as deflocculants or dispersing agents for particulate materials. These polymers, therefore, could not be considered suitable for producing the particulate-based additive conforming to the various objects of the present invention.

V. Surface-Modifiers

Polymers and surfactants are often used in modifying particle surfaces to achieve various properties, including the properties that provide for interparticle repulsion. It has been found that polymers, when adsorbed on particle surfaces, in an amount sufficient to cover more than 50% of the particle surface area, generally enable the particles to mutually repel one another due to what is called "steric repulsion" in colloid literature. If these polymers are ionic, their adsorption on surfaces imparts an electrical charge to the surfaces, which in turn leads to an electrostatic repulsion between the coated-surfaces, since the surfaces carry a like ionic charge.

Traditionally, clay platelets have been modified to produce what is known in the prior art as "organoclays" by treating them with quaternary surfactants that can adsorb on the clay-surface via ion exchange (for example, as described in U.S. Pat. Nos. 5,075,033, 5,164,433, 5,358,562, 5,407,477, and 5,634,969). Modification of clays by adsorbing linear synthetic polymers has also been achieved in the prior art (e.g., see U.S. Pat. No. 5,721,306).

When using either a non-ionic polymer (e.g, polyvinyl alcohol) or a polyelectrolyte (ionic polymer) for modifying the surface of clay to be used as a thickener, the molecular weight, the molecular structure or shape, and the charge density of the polymer are important considerations. This is because the large spatial expansion of a high molecular weight, linear polymer (e.g., polyvinyl alcohol, polyacrylate, polystyrene sulfonate) may lead to a long-range steric repulsion that may oppose thickening. Additionally, a polyelectrolyte (e.g., polyacrylate) with a high charge density when adsorbed on the surface of dispersed particles may produce a strong electrostatic repulsion between the particles, which again may not be favorable for thickening. Also, a polyelectrolyte with a high charge density may be able to maintain flexible, coil-like conformation that supports strong, long-range steric repulsion, over a wide range of ionic strength, thus making it difficult for an added electrolyte to induce interparticle associations required for thickening. Furthermore, for example, an anionic polyelectrolyte with a relatively high charge density, may experience a strong repulsion from a particle that already has an anionic surface charge and, therefore, it may be impossible for such an anionic surface-modifier to adsorb onto a particle surface that carries a like charge. Additionally, a polyelectrolyte having a higher charge density, is likely to have a higher "hydrophilicity", and therefore a lower affinity for hydrophobic surfaces, such as the surface of an oil droplet in an emulsion.

Yet another object of the present invention, therefore, is to use particular macromolecules as dispersants for the particulate materials contained in the disclosed multifunctional additive for cosmetic compositions, that avoid the above-described complexities associated with the use of polymeric surface modifiers. A related object is to identify and use those macromolecular surface-modifiers that can provide for emulsifier/stabilizer functionality.

It would be beneficial to cosmetic formulators to have a multifunctional additive that not only serves as a thickener/gellant but also offers one or more additional features, such as enhancement of UV-protection, antioxidant functionality, humectancy, reduced skin irritation, and consumer perception-related values such as "natural additive". A further object of the present invention, therefore, is to select and use macromolecular reagents for the surface modification of particles contained in the additive of the present invention, which could provide one or more of the foregoing benefits.

VI. Natural Polymers as Surface-modifiers

Natural anionic polymers such as lignin, lignosulfonate, humate, and tannate adsorb on various particle surfaces, both hydrophilic and hydrophobic, and serve as dispersants or deflocculants or emulsifiers/stabilizers for these particles in suspensions or emulsions. These anionic polymers, essentially polyphenols, have a variety of functional groups including polarizable groups (that favor van-der-Waals interaction-driven adsorption) such as phenolic, catecholic, and other aromatic groups, as well as hydrogen bond-forming groups such as phenolic, hydroxyl, carboxylic, and carbonyl groups. Their molecular weight may vary from about 2,000 to about 200,000 or higher. Because of their functional groups and structural properties, these macromolecules can attach onto a variety of substrates via mechanisms such as hydrogen bonding, van der Waals, electrostatic, and hydrophobic interactions, as well as surface-complexation with multivalent cations such as calcium, aluminum, and magnesium. Being polyphenols, they are expected to serve as antioxidants.

Although lignin and lignosulfonate may be regarded as high molecular weight, anionic polymers, their conformations differ vastly from those of linear polymers in that they are highly cross-linked, network polymers having a molecular shape that is often described as being spherical. When adsorbed on a surface or an interface, they can stabilize suspended particles against coagulation via both electrostatic and steric repulsions. However, because of their near-spherical shape, the spatial range of steric repulsion that they provide is not as long as that found with a linear, high molecular weight polymer.

Humate polymers are known to undergo coil-to-globule transformations (an effect that reduces the spatial range of steric repulsion instilled by an adsorbed macromolecule) in the presence of electrolytes. The electrolyte concentrations where such transformations would occur may be expected to be lower for humates than for synthetic polyelectrolytes such as polyacrylates, or polystyrene sulfonates or polynapthalene sulfonates, having anionic charge densities that are inherently higher than that of humates. It should be noted that in humates, the anionic groups, such as phenolate and carboxylate groups, are sparsely distributed in their molecular structure, consisting primarily of aromatic rings, as opposed to in every monomeric repeat unit of a polymer. In accordance with one important embodiment of the present invention, therefore, a humate polymer promotes deflocculation (exfoliation) of smectite clays into their individual platelets and/or into thin stacks of platelets (tactoids) under an applied shear. Once a large number of suspended platelets and/or tactoids are made available, an electrolyte is added at a dosage where it brings about such association between the neighboring delaminated platelets, that produces thickening of the slurry, avoiding the strong face-to-face association between the platelets. Suitable electrolytes are, for example, sodium chloride and potassium chloride.

The use of lignins, lignosulfonates, humates, and tannates as dispersants, emulsifiers/stabilizers, and surface-modifiers has been disclosed in the prior art in connection with numerous industrial applications. These include drilling fluids, oil well cementing, dyes and paints involving organic and inorganic particulates, concrete, gypsum, ceramics and bricks, paper-sizing, wax, drilling fluid, and asphalt emulsions, binding and briquetting aids, and flotation reagents. In the studies that led to the present invention, natural polymers selected from the lignosulfouates, lignins, and humates were evaluated as dispersants for particulate gellants (e.g. smectite clays) and particulate UVR-filter materials to be used in cosmetic formulations. These polyphenolic natural, surface-modifiers, that can serve as antioxidants, have been found in the present invention to be instrumental in providing unexpected combination of properties to personal care and cosmetic compositions, including thickening, SPF enhancement, and emulsification/stabilization.

VII. Process for Making the Multifunctional Additive

In the prior art, surface-modified clays have been made using two processes that are basically as follows. In the first process, a surface-modifying reagent is added to an aqueous clay-slurry and the resulting mixture is agitated for a given period of time during which the reagent is allowed to "react" (e.g., ion-exchange) with the clay surface. After completion of the reaction, the slurry is filtered, and the filter cake dried and pulverized to produce the modified clay. In the second method, the clay is extruded along with the surface-modifying reagent, followed by drying and pulverizing of the extruded material. Clearly, in these processes, several costly unit operations, such as drying and pulverizing, are required. Also, in order to realize the functional properties (e.g., thickening) that require adequate delamination of the clay-platelets or good dispersion of any other co-existing particulate, the particulate-based products made by the foregoing processes would have to be incorporated into personal care or cosmetic formulations using high-shear mixing processes. An important feature of one embodiment of the manufacturing method of the present invention is, therefore, to produce a surface-modified particulate-based additive for personal care or cosmetic formulations in a manner and form that allow one or more of the aforementioned costly processing steps to be avoided, and provide for a great degree of simplicity and ease in incorporating the additive into personal care, cosmetic, and pharmaceutical formulations.

SUMMARY OF THE INVENTION

The present invention is directed to cosmetic, personal care, and topical pharmaceutical compositions, and additives therefor. More specifically, it is related to cosmetic, personal care, and topical pharmaceutical formulations that include an effective amount of a multifunctional additive composition, added as a component in these formulations, said additive improving the SPF (Sun Protection Factor) of these formulations containing inorganic and/or organic sunscreens, and providing at least one of the following additional functional benefits to the formulations:

i) thickening of hydrophilic solvents such as water, glycols, glycerine, alcohols, or mixtures of these solvents;

ii) emulsification/stabilization; and iii) antioxidancy.

In accordance with a preferred embodiment of the present invention, cosmetic and personal care compositions, requiring one or more of the functional properties listed above, can be manufactured using the multifunctional-additive compositions of the present invention. Such an additive preferably contains one or more particulate-based thickeners, such as a smectite clay, colloidal silica, laponite, and/or alumina, and most preferably one or more smectite clays. According to one important embodiment of the present invention, the thickener particles are co-dispersed with particles of one or more particulate UVR-filters such as titanium dioxide, zinc oxide, or SUNSPERE (available from International Specialty Chemicals, ISP), and most preferably with the natural particulate sunscreens such as the metal oxides. Another important component of the multifunctional-additive compositions is a dispersant or surface-modifier for the foregoing particulate materials, selected from the family of polyphenolic, natural polymers such as lignosulfonates, lignins, humates, tannates, and derivatives thereof. In addition, these compositions optionally include one or more of the following components: electrolytes, defoamers, humectants, emollients for cosmetics, preservatives, whiteners, and the like.

A hydrogel is the most preferred form of the disclosed multifunctional-additive, where the particulate-based thickener and the UVR filter material(s) are dispersed in an aqueous medium that may contain one or more hydrophilic organic solvents such as glycols, glycerine, and/or alcohols. As for an essential component, the hydrogel also contains one or more dispersing or surface-modifying agent selected from the group of polyphenolic, natural polymers such as lignosulfonate, lignin, and humate, to ensure good dispersion and colloidal stability of the particulate material(s) contained in the hydrogel. The hydrogel form is preferred since the composition can be easily blended into a cosmetic formulation containing any additional functional ingredient (for example, an organic sunscreen), without requiring an excess of shear. Any high shear equipment, for example, a homogenizer, or colloid mill, or other types of batch or in-line high shear mixer can be used to produce the hydrogel. Alternatively, the compositions of the present invention may be produced in a powder form, wherein the particle-surfaces of the thickener and/or the UVR-filter material are pre-treated and surface-modified with the natural polymer, and then dried, e.g., to 10% by weight liquid, or less. As yet another way of producing the compositions of the present invention, the particulate-based thickener and/or the particulate UVR-filter, and the foregoing natural polymer-based dispersant, may be added individually as components of a cosmetic formulation intended to contain the particulate material(s) as being dispersed in a hydrophilic solvent.

According to a preferred method of making the multi-functional additives of the present invention, in the form of a slurry-based additive-concentrate (e.g., hydrogel), a mixture of a smectite clay and a particulate UVR-filter ($TiO_2$ or ZnO) is added to an aqueous solution of the natural polymer (e.g., lignosulfonate), containing the dispersant at a dosage in the range of about 0.05–300% based on the total dry weight of the clay and the particulate UVR-filter, more preferably about 5–50% based on the dry weight of the particulate materials, and most preferably about 10–30% based on the dry weight of the particulate materials. The amount of clay and particulate UVR-filter material added is preferably in the range of about 1–65% by weight, based on the total weight of the slurry. The weight ratio of clay and $TiO_2$ in the clay-$TiO_2$ mixture is preferably in the range of 1:1 to 9:1, or in some cases, no $TiO_2$ is used, or in other cases, no clay is added. The clay-$TiO_2$ mixture is added incrementally while a solution of the natural polymer dispersant is kept under agitation. After the entire amount of particulate mixture has been added to the natural polymer solution, mixing is continued until the resulting slurry assumes a homogeneous texture i.e., free of clay lumps. The slurry is then fed to a high-shear/impact device, such as a pressure homogenizer, a colloid mill or other such devices. Upon passing through the high shear/impact device once, the slurry turns into a highly viscous, gel-like material that is referred to herein as a mastergel. Optionally, the slurry may be passed through the high shear/impact device for more than one time, preferably for two to three times.

The most preferred method of making the mastergel involves the following sequential steps: i) a particulate UVR-filter ($TiO_2$ or ZnO) is added to an aqueous solution of the natural polymer (e.g., lignosulfonate); ii) the resulting slurry is homogenized in a high shear/impact device (e.g., rotor-stator mixer) for about 5–10 minutes; iii) smectite clay is added incrementally to the homogenized slurry of the UVR-filter while the slurry is kept under low-shear agitation using a paddle mixer or the like; and iv) the resulting mixture is fed to and passed through a high shear/impact device (e.g., pressure-homogenizer, colloid mill) for one to three times. The aqueous solution of the dispersant contains the dispersant at a dosage in the range of about 0.05–300% based on the total dry weight of the particulate materials, more preferably about 5–50% based on the dry weight of the particulate materials, and most preferably about 10–30% based on the dry weight of the particulate materials. The amount of clay and particulate UVR-filter material added is preferably in the range of about 1–65% by weight, based on the total weight of the slurry.

The mastergel can be subsequently diluted in a desired hydrophillic solvent using a mixer, before or during the preparation of a cosmetic product. It may be noted that in a preferred embodiment, a water-content of at least about 8%, preferably about 10% to about 30% by weight, based on the total weight of the natural polymer (e.g., lignosulfonate/lignin/humate) solution, is provided for one or more of these natural polymers to completely dissolve in solvents containing predominantly hydrophilic organic solvents such as glycols, glycerine, and/or alcohols.

It has been found that the dispersing effect of the natural polymer, e.g., lignosulfonate, could not be realized adequately when attempts were made to produce the mastergel in predominantly glycol-containing mixtures of glycol and water. For example, a clay-content of 20%, based on the total weight of the slurry, was required to make a mastergel having a Brookfield viscosity of 24,150 cps (@ 20 rpm) in 75:25 ethylene glycol-water mixture. This finding led the inventors herein to the aforementioned "aqueous mastergel" approach for rendering clay as an effective thickener, even for hydrophilic organic solvents used in personal care and cosmetic compositions.

As used herein, the word "particulate" refers to any organic or inorganic material so long as it is available as solid or liquid particles that do not dissolve in hydrophilic liquids, such as water, a hydrophilic organic liquid, and mixtures thereof, included as a component in the compositions of the present invention. Particulate further refers to any organic or inorganic material so long as it is contained in the foregoing compositions in the form of solid or liquid particles dispersed or emulsified in a hydrophilic liquid. Any particulate material that is either a thickener or a UVR-filter is useful in accordance with the present invention so long as it has a particle size distribution such that at least 90% of the particles have a size less than or equal to 30 microns. Preferably, at least 90% of the particles of the particulate adsorbent/absorbent material are colloidal in size (<1 micron).

Although the natural polymer-based dispersants or surface-modifiers contained in the aqueous mastergel are non-gum and non-cellulosic natural polymers, the mastergel may contain one or more additional thickening agents besides swellable layered silicates, including gums and cellulosics, as well as proteins and polyacrylates. The amount of such a gellant may vary from about 0.1–5% of the weight of the mastergel. Additionally, the mastergel may also contain functional oils, dispersed as emulsion droplets, at a maximum amount of about 50% of the weight of the mastergel. Such oils, offering functional benefits to cosmetic products, include but are not limited to silicone oils, and vegetable or botanical or flower oils.

Any lignosulfonate, kraft lignin, sulfonated kraft lignin, oxylignin, sulfonated oxylignin, humate, sulfonated humate, tannate and/or sulfonated tannate as salts can be used as a natural polymer dispersant or surface-modifier. For the lignosulfonate and lignin, both hardwood and softwood lignosulfonate/lignin may be used. As used herein, "kraft lignin" and "lignosulfonate" have their normal connotation, respectively, referring to the substance typically recovered from alkaline pulping liquor and the substance typically recovered from sulfite pulping process. On the other hand, humate refers to water-soluble salts of humic acid polymers. The most preferred dispersants include ultrafiltered or otherwise de-sugared lignosulfonate, oxylignin or oxylignin sulfonate, and humate as sodium salts. The preferred molecular weight of these dispersants is in the range 5,000–100,000. Examples of some preferred lignosulfonate and humate products for producing the additive disclosed herein include Ultrazine NAC, Vanisperse A, Maracell XC-2 (sodium lignosulfonates from Borregaard LignoTech, BLT), Borresol HA-2 (a potassium humate from BLT, but used in the sodium-form after base-exchanging), and Enersol SC (a sodium humate from American Colloid Company).

Derivatives of the foregoing natural polymers that are useful in making the multifunctional additive of the present invention include the following:

oxidized (for example, using air, ozone, and/or hydrogen peroxide) lignosulfonate or oxidized lignin;

co-polymers of lignosulfonate or of lignin with acrylate, acrylamide, styrene sulfonate, and napthalene sulfonate derivatives;

azolignosulfonate and azolignin;

formaldehyde condensate of lignosulfonate or of lignin or of humate or of tannate;

hydrophobically-modified lignosulfonate, lignin, humate, or tannate;

cationically-modified lignosulfonate, lignin, humate, or tannate;

amino lignosulfonates or amino lignins; and alkylated and/or crosslinked lignosulfonate or alkylated and/or crosslinked lignin.

The hydrophilic solvent may be selected from the group consisting of any hydrophilic organic solvent, water, and mixtures. Preferred hydrophilic solvents have a hydroxyl or polyhydroxyl functionality, such as an alcohol, a glycol, polyglycol, glycerol, and the like. The alcohols can be monohydric alcohols or polyhydric alcohols that are linear or branched.

The ranges of proportions of the various key ingredients included in mastergel (or additive-concentrate) compositions are given in Table I, based on the total weight of the mastergel. It should be noted, however, that in accordance with one embodiment of the present invention, the additive-concentrate would invariably contain one or more particulate material. The preferred dosage range of mastergel compositions for incorporation into a cosmetic formulation is 0.5–100% by weight, based on the weight of the formulation. However, in accordance with an important embodiment of the present invention, cosmetic and personal care formulations can be manufactured by adding in the key ingredients listed in Table I, individually as components of the formulations. For such compositions of the present invention, the dosage of each of the ingredients will be at per with that calculated based on proportions of ingredients in mastergel compositions as shown in Table I and the aforementioned preferred mastergel dosage.

TABLE I

| Key Ingredient Functionality | Preferred Key Ingredient | Proportion by Weight based on the Weight of Mastergel |
|---|---|---|
| Thickener | Smectite Clays | 0–65% |
| Particulate UVR-Filter | $TiO_2$ and ZnO | 0–65% |
| Natural Polymer Dispersant | Lignosulfonate, Lignin, Humate | 0.05–60% |
| Dispersion Medium | Water, Hydrophilic Organic Solvents | 35–90% |
| Thickener Supplement | Gelatin, Gums, Polyacrylates | 0–5% |
| Functional Oils | Vegetable and botanical oils, Silicone oils, Organic Sunscreen | 0–40% |

In order to illustrate the present invention clearly, the following data are presented. The following examples and data are included as illustrations of the invention and should not be construed as limiting the scope of the invention.

EXAMPLE 1

This example shows that, as compared to a linear polymer, such as a polyacrylate, lignosulfonate and humate-based dispersants/surface modifiers allow a higher level of thickening to be attained in smectite clay dispersions, while improving the stability of these dispersions against strong coagulation.

The colloidal stability of concentrated dispersions may be assessed from their viscosity, inasmuch as a lower viscosity indicates a more stable dispersion with particles that are deflocculated to a greater extent. Accordingly, a slurry may be characterized to have a low colloidal stability, if its viscosity increases rapidly with time. The addition of an electrolyte tends to reduce the electrostatic repulsion between the suspended particles with like electrical charge on their surfaces, implying that an added electrolyte may promote coagulation for such particles. Considering the above, stability- testing of smectite clay dispersions was carried out by measuring their viscosity using a Brookfield viscometer. This included tests for the evaluation of electrolyte-stability in the presence and absence of dispersants.

A 17-gram sample of a sodium bentonite (Polargel NF from American Colloid Company, ACC) was added to a dispersant solution containing 183 grams of water, a given amount of a dispersant, and in some cases certain amounts of an electrolyte, sodium chloride (NaCl), and a defoamer. The resulting slurry was homogenized in a Waring blender at "high" speed (22,000 rpm) for a total mixing time of 4 minutes. The slurry was then transferred to a plastic cup and degassed under vacuum. The Brookfield-viscosity of the slurry was recorded at various times measured from the time of completion of degassing. The results of these slurry viscosity tests are shown in Table II, with the "control" test indicating that no dispersant was used in the test. Degassing was not carried out for the control tests, and the time periods for the measurement of slurry-viscosity are counted from the time of completion of homogenization.

TABLE II

| Test # | Dispersant | Dispersant Dosage, % on clay | Time, hr. | Brookfield Viscosity 10 rpm | Brookfield Viscosity 20 rpm |
|---|---|---|---|---|---|
| | | No salt added | | | |
| 1 | Control | 0 | 0.25 | | 3,760 |
| | | | 72 | | 7,000 |
| 2 | Vanisperse A (sodium lignosulfonate) | 10 | 0.25 | | 2,700 |
| | | | 192 | | 3,800 |
| | | | 336 | | 3,400 |
| 3 | Borresol HA-2 (sodium humate) | 10 | 0.25 | | 1,000 |
| | | | 192 | | 2,700 |
| | | | 336 | | 3,000 |
| 4 | Polyacrylate Mw = 8,000 (sodium salt) | 10 | 0.25 | | 250 |
| | | | 192 | | 400 |
| | | | 336 | | 400 |
| | | 0.2 g of NaCl added | | | |
| 5 | Control | 0 | 0.25 | | 14,200 |
| | | | 96 | | 15,800 |
| 6 | Vanisperse A | 10 | 0.25 | | 2,600 |
| | | | 96 | 6,200 | 3,300 |
| | | | 336 | 7,000 | 3,700 |
| 7 | Borresol HA-2 | 10 | 0.25 | | 900 |
| | | | 96 | 2,800 | 1,800 |
| | | | 336 | 3,200 | 2,300 |
| 8 | Polyacrylate Mw = 8,000 | 10 | 0.25 | | 150 |
| | | | 96 | 400 | 300 |
| | | | 336 | 600 | 500 |
| 9 | Polyacrylate Mw = 32,000 | 10 | 0.25 | | 500 |
| | | | 96 | 1,200 | 700 |
| | | | 336 | 1,200 | 700 |
| 10 | Borresol HA-2 | 30 | 0.25 | | 500 |
| | | | 192 | 2,200 | 1,200 |
| | | | 336 | 2,400 | 1,400 |
| 11 | Vanisperse A | 30 | 0.25 | | 2,000 |
| | | | 192 | 5,400 | 3,000 |
| | | | 336 | 5,600 | 3,000 |
| 12 | Polyacrylate Mw = 8,000 | 30 | 0.25 | | 500 |
| | | | 192 | 1,200 | 700 |
| | | | 336 | 1,200 | 800 |
| | | 1.5 g of NaCl added | | | |
| 13 | Control | 0 | 0.25 | | 16,400 |
| | | | 192 | 35,200 | 18,000 |
| | | | 336 | 33,000 | 17,500 |
| 14 | Vanisperse A | 10 | 0.25 | | 2,700 |
| | | | 192 | 5,800 | 3,600 |
| | | | 336 | 6,000 | 3,700 |
| 15 | Polyacrylate Mw = 8,000 | 10 | 0.25 | | 250 |
| | | | 192 | 2,000 | 1,400 |
| | | | 336 | 2,000 | 1,700 |

EXAMPLE 2

This example shows that a lignosulfonate-based dispersant/surface modifier, which can improve the colloidal stability of smectite clay dispersions, can also serve as an effective dispersant (or deflocculant) for titanium dioxide ($TiO_2$) such that a single dispersant can be used to enhance the stability of a dispersion containing both clay and $TiO_2$.

A 65-gram sample of pigment-grade $TiO_2$ (obtained from Whittaker, Clark, & Daniels, Inc.) was added to a dispersant solution in a Waring blender, containing a given amount of a dispersant. The $TiO_2$ used has the crystal structure of the anatase form of $TiO_2$. For this pigment-grade $TiO_2$ material, the average primary particle size is 0.3 micron, and the maximum particle size is 1 micron, as specified by the supplier. In all cases, the dispersant solution contained 120 gram of deionized water, and 0.7 gram of NaCl, while in some cases it further contained a defoamer. The slurry was homogenized for 4 minutes, following which it was transferred to a plastic cup. The slurry-viscosity was measured after 20 minutes from the time of completion of homogenization. The results of these slurry viscosity tests are presented in Table III.

TABLE III

| Test # | Dispersant | Dispersant Dosage, % on $TiO_2$ | Slurry pH | Brookfield Viscosity 10 rpm |
|---|---|---|---|---|
| 1 | Control | 0 | 7.5 | 5,500 |
| 2 | Vanisperse A | 10 | 7.2 | 950 |
| 3 | Vanisperse A | 15 | 7.4 | 700 |
| 4 | Vanisperse A | 20 | 7.5 | 500 |
| 5 | Vanisperse A | 25 | 7.5 | 300 |
| 6 | Vanisperse A | 30 | 7.5 | 300 |
| 7 | Polyacrylate (Sokalan PA 30CL, from BASF Corp.) Mw = 8,000 | 10 | 7.3 | 3,100 |
| 8 | Polyacrylate | 20 | 7.3 | 2,650 |
| 9 | Polyacrylate | 25 | 7.3 | 2,400 |

A significantly lower viscosity was attained in an aqueous slurry of $TiO_2$, when it contained the lignosulfonate, Vanisperse A, indicating a strong dispersing effect of the lignosulfonate on $TiO_2$. On the other hand, polyacrylate fell short of Vanisperse A in dispersing $TiO_2$, although it was found (see Example 1) to be a good dispersant for a smectite clay.

EXAMPLE 3

This example illustrates that making an aqueous mastergel and subsequently diluting it in propylene glycol-water mixtures is a more effective way of achieving the thickener functionality of clay in these mixed solvents.

The method used for the tests, the results of which appear in Table IV, is described below. A known weight (5% based on the weight of clay) of a sodium-lignosulfonate (Wanin S, Mol. wt.=54,000) was dissolved in a given amount of a propylene glycol-water mixture in a Waring blender. Subsequently, a measured amount of a sodium bentonite (Polargel NF) was added to the dispersant solution. The slurry was homogenized in the blender at "low" speed (18,000 rpm) for the first 30 seconds and then at "high" speed (22,000 rpm) for the rest of a total mixing time of 10 minutes. The slurry was then transferred to a plastic cup for Brookfield viscosity measurements. The slurry-viscosity was measured 10 minutes (for Tests 1–5) and 15 minutes (for Tests 5 and 6) after completion of homogenization. In Table IV, the grades 1 through 3 indicate the extent of syneresis (after overnight standing), with the greatest amount of syneresis being grade 3.

TABLE IV

| Test # | % Clay | % Propylene Glycol | % Water | Brookfield Viscosity @ 20 rpm, cps | Syneresis |
|---|---|---|---|---|---|
| 1 | 8.36 | 0 | 91.64 | 5,880 | None |
| 2 | 8.36 | 18.33 | 73.31 | 3,820 | None |
| 3 | 8.36 | 45.82 | 45.82 | 130 | 1 |
| 4 | 8.36 | 64.15 | 27.49 | 75 | 2 |
| 5 | 8.36 | 73.31 | 18.33 | 50 | 3 |
| 6 | 10 | 63 | 27 | 200 | 1 |
| Control | 10 | 63 | 27 | 460 | 3 |

It is apparent from the results presented in Table IV that the dispersing role of lignosulfonate cannot be fully utilized in propylene glycol-enriched solvents if the dry clay is added directly to lignosulfonate-solutions in such solvents.

In contrast, Table V shows that an aqueous mastergel, containing sodium-lignosulfonate (Ultrazine NAC, Mol. wt.=70,000) as the-clay-dispersant, can yield reasonably high slurry-viscosity even when diluted in propylene glycol-water mixtures to relatively low clay-contents (Tests 1 through 4). The table also includes the results for the control tests where a mastergel containing no dispersant was diluted in propylene glycol. It is evident from Tests 5 and Control #1 that a significantly higher level of thickening can be obtained from the use of lignosulfonate-modified clay as opposed to the unmodified clay.

In Table V, the proportions of the various slurry-components are expressed as percentages of the total weight of the slurry, while the weight of dispersant is 10% based on the weight of clay. Dilution of the mastergel in propylene glycol involved weighing out desired amounts of propylene glycol and water, if needed, in a Waring blender, adding the required amount of the mastergel to the glycol, and then homogenizing the slurry for a total mixing time of 4 minutes at 22,000 rpm.

TABLE V

| Test # | % Clay | % Prop. Glycol | % Water | Time, Hr. | Brookfield Viscosity, Cps 10 rpm | 20 rpm | Syneresis after 6–7 days of standing |
|---|---|---|---|---|---|---|---|
| 1 | 2.3 | 82 | 15.4 | 1 | 2,560 | 1,520 | Slight hint-hardly discernible |
|   |     |    |      | 24.72 | 3,190 | 1,962.5 | |
| 2 | 2.3 | 78.2 | 19.3 | 1 | 2,080 | 1,250 | Slight hint-hardly discernible |
|   |     |      |      | 23.72 | 2,580 | 1,600 | |
| 3 | 2.3 | 68.4 | 29.1 | 1 | 975 | 615 | Slight hint-hardly discernible |
|   |     |      |      | 24.72 | 1,420 | 880 | |
| 4 | 4.3 | 67 | 28.4 | 1 | 4,410 | 2,400 | Slight hint-hardly discernible |
|   |     |    |      | 24.88 |       | 2,925 | |
| 5 | 6.4 | 50 | 42.9 | 2 | 8,980 | 4,950 | Slight hint-hardly discernible |
|   |     |    |      | 27.88 | 9,600 | 5,110 | |
| Control-1 | 6.3 | 50 | 43.7 | 2 | 5,540 | 3,210 | Slight hint-hardly discernible |
|   |     |    |      | 27.88 | 4,800 | 2,650 | |
| Control-2 | 2.3 | 82 | 15.7 | 1 | 2,350 | 1,412.5 | Slight hint-hardly discernible |
|   |     |    |      | 23.72 | 3,130 | 1,930 | |

EXAMPLE 4

This example shows the effects of lignosulfonate and humate on the viscosity of aqueous slurry of laponite (obtained from Southern Clay Company, Inc.), a synthetic layered silicate material composed of sodium-magnesium-lithium silicate.

A 6-gram sample of Laponite was added to a dispersant solution containing 192.76 grams of deionized water. The resulting slurry was homogenized in a Waring blender for 5 minutes at the maximum speed (22,000 rpm). The slurry was then transferred to a plastic container, degassed, and measured for viscosity. Table VI shows the results of such slurry-viscosity tests for various dispersants.

TABLE VI

| Test # | Dispersant | Dispersant Dosage, % on Laponite | Time, hr. | Brookfield Viscosity 10 rpm | 20 rpm |
|---|---|---|---|---|---|
| 1 | Control | 0 | 0.25 | Free Flowing | |
| 2 | Vanisperse A | 20 | 0.25 | 20,000 | 13,200 |
| 3 | Vanisperse A | 30 | 0.25 | 9,600 | 8,200 |
| 4 | Vanisperse A | 60 | 0.25 | 3,400 | 1,700 |
| 5 | Borresol-HA2 (sodium humate) | 20 | 0.25 | 13,600 | 7,000 |
| 6 | Borresol-RA2 (sodium humate) | 60 | 0.25 | 8,800 | 4,400 |
| 7 | Polyacrylate Mw = 8,000 | 60 | 0.25 | 760 | 500 |

EXAMPLE 5

This example describes a method for making the hydrogel material that can be used as an additive in cosmetic formulations.

In 694.44 g of de-ionized water was dissolved 32.15 g of Vanisperse A (sodium lignosulfonate), 8.07 g of Maracell XC-2 (sodium lignosulfonate), and 16 g of Borresol HA-2 (as sodium humate), using an industrial blender. To the resulting dispersant solution were added 5.6 g of a defoamer (Dow Corning 2210 antifoam), and 4.8 g of glydant (preservative). A mixture of 160 g of sodium bentonite (Polargel NF) and 107.2 g of $TiO_2$ (pigment-grade) was then added to the dispersant solution. The resulting slurry was homogenized in the industrial blender for a period of 20 minutes at 18,000 rpm. The Brookfield viscosity of the gel thus produced, as measured after 0.25 hours from the time of completion of homogenization, is 72,000 cps.

EXAMPLE 6

This example shows that the Sun Protection Factor (SPF) due to an organic sunscreen, octyl methoxycinamate, is enhanced when the mastergel materials (smectite clay-based gellant) disclosed herein, are used as an additive in a sunscreen formulation. The method of preparing sunscreen emulsions, and some exemplary compositions of the emulsions used for the evaluation of SPF are given below.

| Sample | Phase | Ingredient | Function | % By Wt. |
|---|---|---|---|---|
| Emulsion #1 | A | Dionized Water | Hydrophilic carrier | 32.36 |
|  | A | Propylene Glycol | Humectant | 2.5 |
|  | A | Keltrol T (2%) | Thickener | 15.0 |
|  | A | Clay-based Gellant (28.22% solids) | Thickener | 21.44 |
|  | B | Lipomulse 165 | Emulsifier | 2.0 |
|  | B | Octyl Methoxycinamate | Suncreen active | 7.5 |
|  | B | Lipowax D | Emulsifier | 4.0 |
|  | B | Finsolv TN | Emollient | 10.0 |
|  | B | DC 245 Fluid | Emollient | 5.0 |
|  | C | Glydant | Preservative | 0.2 |
| Emulsion #2 | A | Dionized Water | Hydrophilic carrier | 51.8 |
|  | A | Propylene Glycol | Humectant | 2.5 |
|  | A | Keltrol T (2%) | Thickner | 15.0 |

-continued

| Sample | Phase | Ingredient | Function | % By Wt. |
|---|---|---|---|---|
| | A | TiO₂ | Particulate Sunscreen | 2.0 |
| | A | Clay-based Gellant | Thickener | 0 |
| | B | Lipomulse 165 | Emulsifier | 2.0 |
| | B | Octyl Methoxycinamate (OMC) | Organic Suncreen | 7.5 |
| | B | Lipowax D | Emulsifier | 4.0 |
| | B | Finsolv TN | Emollient | 10.0 |
| | B | DC 245 Fluid | Emollient | 5.0 |
| | C | Glydant | Preservative | 0.2 |

Manufacturing Procedure:
Heat Phase A to 75° C.
Heat Phase B to 75° C.
Add Phase B to Phase A.
Cool to 45° C. and add Phase C.

Homogenize on Silverson homogenizer for 3 minutes @ 5,000 rpm.

The compositions of the clay-based gellants used in making the sunscreen emulsions (each containing 7.5% OMC by weight) for the evaluation of SPF, as well as the measured in-vitro SPF and UVA/UVB ratio for these emulsions are given in Table VII. Gel #1, as noted in Table VII, was used in making Emulsion 1 described above. The SPF measurement was carried out by casting a film of a sunscreen emulsion on a substrate (Vitro-skin) of a given area (application rate 2 microliter/cm²), and then measuring the UV-absorbance of the film in the wavelength range of 290–400 nm. The instrument used in measuring the UV-absorbance is a Labsphere UV Analyzer.

Note that the dispersants used in making Gel #2 and 3 are purified (via ultrafiltration and precipitation) sodium lignosulfonate, while the dispersants used in making Gel #1 include sodium humate and purified sodium lignosulfonate.

A comparison of the SPF values obtained for the clay-based gellant-containing emulsions, with that of the control emulsion (with no clay-based gellant added), shows that the addition of the clay-based gellants to sunscreen emulsions containing 7.5% OMC (w/w) can greatly enhance the SPF of such systems. Also, even though the control emulsion contained TiO₂ at the same level (2%, w/w) as in the three emulsions that contained Gel #1, 2, and 3, respectively, the SPF of the control emulsion fell far below those of the clay-based gellent-containing emulsions. Another beneficial effect of having these gellants as an ingredient in sunscreen emulsions is the increase in the UVA/UVB ratio.

The SPF and UVA/UVB ratio of yet another control emulsion containing 7.5% (w/w) OMC but no clay-based gellant of the present invention, and with ingredients similar to the ones used in making the foregoing emulsions, were 8.9 and 0.21, respectively. Note that all emulsions, including the control emulsions, contained xanthan gum (Keltrol T) as a thickener (which can thicken water by itself), at the level of 0.3% by weight, based on the total weight of the emulsion. This shows that a combination of TiO₂ and a natural polymer such as xanthan gum, as contained in the control emulsion, would not enhance the SPF of an organic sunscreen-containing emulsion.

TABLE VII

| Sample | Wt. % of total solids* | Wt. % of water | Wt. % of clay | Wt. % of TiO₂ | Wt. % of dispersant | % Gellant Dosage on Solids-basis on emulsion | SPF | UVA/UVB |
|---|---|---|---|---|---|---|---|---|
| Gel #1** | 28.22 | 70.87 | 13.98 | 9.34 | 4.9 | 6.05 | 36.5 +/− 4.4 | 0.63 |
| Gel #2 | 32.61 | 64.88 | 15.05 | 10.04 | 7.53 | 6.5 | 25.6 +/− 6.8 | 0.63 |
| Gel #3 | 48.51 | 49.57 | 14.39 | 9.61 | 24.51 | 10.1 | 29.7 +/− 2.7 | 0.6 |
| Control*** | | | | | | | 7.3 +/− 1.5 | 0.49 |

*Excluding the preservative and the defoamer
**Used in Emulsion #1 described above
***Emulsion #2 described above

EXAMPLE 7

This example shows the in-vivo SPF test results for the emulsions (containing 7.5% OMC by weight) corresponding to Gel #1 and Gel #3 shown in Table VII (EXAMPLE 6). The tests were carried out on multiple subjects having skin type II or III. The data presented in Table VIII indicate a close match between the in-vitro and in-vivo SPF test results (See Table VII, EXAMPLE 6, for the in-vitro results).

TABLE VIII

| Sample | Number of Subjects | SPF |
|---|---|---|
| Gel #1 (see Table VII) | 4 | 27.5 |
| Gel #3 (see Table VII) | 3 | 28.7 |

EXAMPLE 8

This example shows the effectiveness of a clay-based gellant with composition similar to Gel #2 shown in Table VII (EXAMPLE 6), in boosting the SPF of an organic sunscreen, for varying dosage of the additive and the organic sunscreen.

Two sets of emulsions, similar to Emulsion #1 described in EXAMPLE 6, were prepared, that contained a portion of a mastergel similar in composition to Gel #2 in EXAMPLE 6, and OMC as the organic sunscreen. The first set of emulsions contained 2% OMC (w/w), while the second set contained 7.5% OMC (w/w). Table IX shows the SPF of the various emulsion samples, measured as per the method described in EXAMPLE 6.

TABLE XI

| Sample | OMC Dosage on the weight of emulsion, % | Gellant Dosage on solids-basis on Emulsion, % | SPF | UVA/UVB |
|---|---|---|---|---|
| Set #1 | | | | |
| 1 | 2 | 0 | 4.5 ± 0.9 | 0.19 |
| 2 | 2 | 1.625 | 7.1 ± 2.1 | 0.36 |
| 3 | 2 | 3.25 | 10.4 ± 1.2 | 0.47 |
| 4 | 2 | 6.5 | 17.4 ± 3.6 | 0.58 |
| Set #2 | | | | |
| 1 | 7.5 | 1.625 | 10.3 ± 0.9 | 0.4 |
| 2 | 7.5 | 3.25 | 13.4 ± 2.8 | 0.49 |
| 3 | 7.5 | 6.5 | 26.0 ± 3.9 | 0.57 |

EXAMPLE 9

This example shows the SPF enhancement effect of the clay-based gellants of the present invention, in liquid makeup, and daily-moisturizer formulations. The gellant compositions are given in Table X, followed by the formulations for the control (with no clay-based gellant) and the test samples.

TABLE X

| Sample | Wt. % of Clay | Wt. % of TiO$_2$ | Wt. % of Dispersant (Lignosulfonate) | Wt. % of Water |
|---|---|---|---|---|
| Gel #1 | 12.72 | 19.08 | 9.6 | 56.31 |
| Gel #2 | 6.93 | 34.63 | 3.48 | 53.25 |

Liquid Makeup Formulations

| Sample | Phase | Ingredient | % By Weight |
|---|---|---|---|
| Emulsion #1 (Control) | A | Deionized Water | 44.85 |
| | A | Tetrasodium EDTA | 0.05 |
| | A | M, P Diol | 2.0 |
| | A | Keltrol T (2%) | 10.0 |
| | A | Clay-based Gellant #1 | 0 |
| | B | Glycerin 96% | 4.0 |
| | B | Deionized Water | 5.0 |
| | B | Triethanolamine 99% | 0.5 |
| | C | Arlacel 165 | 1.5 |
| | C | Trivent DOS | 7.0 |
| | C | Uvinul MC-80 | 5.0 |
| | C | Trivent PE-48 | 5.0 |
| | C | Arlacel 20 | 2.5 |
| | C | Cetearyl Alcohol | 1.0 |
| | C | Stearic Acid | 2.0 |
| | D | Mica MRP | 2.0 |
| | D | Microna Matte White | 4.0 |
| | D | Microna Matte Yellow | 2.0 |
| | D | Microna Matte Orange | 0.2 |
| | D | Microna Matte Red | 0.2 |
| | D | Microna Matte Black | 0.2 |
| | E | Germaben II | 1.0 |
| Emulsion #2 | A | Deionized Water | 34.85 |
| | A | Tetrasodium EDTA | 0.05 |
| | A | M, P Diol | 2.0 |
| | A | Keltrol T (2%) | 10.0 |
| | A | Clay-based Gellant #1 (41.39% Functional Solids) | 10.0 |
| | B | Glycerin 96% | 4.0 |
| | B | Deionized Water | 5.0 |
| | B | Triethanolamine 99% | 0.5 |
| | C | Aracel 165 | 1.5 |
| | C | Trivent DOS | 7.0 |
| | C | Uvinul MC-80 | 5.0 |
| | C | Trivent PE-48 | 5.0 |
| | C | Arlacel 20 | 2.5 |
| | C | Cetearyl Alcohol | 1.0 |
| | C | Stearic Acid | 2.0 |
| | D | Mica MRP | 2.0 |
| | D | Microna Matte White | 4.0 |
| | D | Microna Matte Yellow | 2.0 |
| | D | Microna Matte Orange | 0.2 |
| | D | Microna Matte Red | 0.2 |
| | D | Microna Matte Black | 0.2 |
| | E | Germaben II | 1.0 |

Manufacturing Procedure:

Combine Phase A at 75° C.

Add Phase B

Heat Phase C to 75° C. and add to batch.

Combine Phase D and add to batch.

Cool to 40° C. and add Phase E.

Mix using a propeller type of agitator until uniform.

Daily Moisturizer Formulations

| Sample | Phase | Ingredient | % By Weight |
|---|---|---|---|
| Emulsion #3 (Control) | A | Deionized Water | 30.60 |
| | A | Disodium EDTA | 0.10 |
| | A | M, P Diol | 1.5 |
| | A | Keltrol T (2%) | 20.0 |
| | A | Carbopol 980 (2%) | 20.0 |
| | A | Clay-based Gellant #2 | 0 |
| | B | DC 245 | 5.0 |
| | B | Cetyl Alcohol | 0.5 |
| | B | Brij 721 | 1.5 |
| | B | Finsolv TN | 2.5 |
| | B | Trivent OP | 5.0 |
| | B | Uvinul MC-80 | 7.5 |
| | B | Serasynt SD | 1.0 |
| | B | DC 200-100 | 1.0 |
| | B | Stearic Acid | 1.5 |
| | B | Vitamin A Palmitate | 0.1 |
| | B | Vitamin E Acetate | 0.2 |
| | C | Triethanolamine | 0.8 |
| | D | Fragrance | 0.2 |
| | E | Germaben II | 1.0 |
| Emulsion #4 | A | Deionized Water | 25.60 |
| | A | Disodium EDTA | 0.10 |
| | A | M, P Diol | 1.5 |
| | A | Keltrol T (2%) | 20.0 |
| | A | Carbopol 980 (2%) | 20.0 |
| | A | Clay-based Gellant #2 | 5.0 |
| | B | DC 245 | 5.0 |
| | B | Cetyl Alcohol | 0.5 |
| | B | Brij 721 | 1.5 |
| | B | Finsolv TN | 2.5 |
| | B | Trivent OP | 5.0 |
| | B | Uvinul MC-80 | 7.5 |
| | B | Serasynt SD | 1.0 |
| | B | DC 200-100 | 1.0 |
| | B | Stearic Acid | 1.5 |
| | B | Vitamin A Palmitate | 0.1 |
| | B | Vitamin E Acetate | 0.2 |

-continued

Daily Moisturizer Formulations

| Sample | Phase | Ingredient | % By Weight |
|---|---|---|---|
| | C | Triethanolamine | 0.8 |
| | D | Fragrance | 0.2 |
| | E | Germaben II | 1.0 |

Manufacturing Procedure:

Heat Phase A to 75° C.

Heat Phase B to 75° C.

Add Phase B to Phase A.

Add Phase C

Cool to 40° C. and add remaining phases.

Homogenize on Silverson homogenizer for 2 minutes @ 6,000 rpm with large head.

The SPF and UVA/UVB ratio of the emulsion samples described above are given in Table XI.

TABLE XI

| Sample | SPF | UVA/UVB Ratio |
|---|---|---|
| Emulsion #1 | 21.2 ± 1.7 | 0.44 |
| Emulsion #2 | 40.3 ± 3.3 | 0.58 |
| Emulsion #3 | 8.5 ± 0.6 | 0.28 |
| Emulsion #4 | 13.3 ± 2.4 | 0.48 |

EXAMPLE 10

This example demonstrates that the dispersant(s) used in producing the clay-based gellants are instrumental in realizing the SPF enhancement effect of the additive.

Various O/W emulsions, with some of them containing the clay-based gellants, were tested for SPF. In terms of ingredients, these emulsions are akin to the ones described in EXAMPLE 6, except that some of these emulsions contained the sunscreen active, avobenzone, for which phenonip was used as the preservative. Also, one of the avobenzone-containing emulsions (Emulsion 8 in Table XII) did not receive any addition of emulsifiers such as Lipomulse 165 and Lipowax D. The in vitro SPF test results are presented in Table XII. Emulsions 4, 5, 6, and 8 were prepared by incorporating portions of clay-based gellants in the water-phase of the emulsions. Unlike the clay-based gellants of the present invention, used in making emulsions 5, 6, and 8, the clay-based gellant used in making emulsion 4 did not contain any linosulfonate as the particulate dispersant. The relative proportions of smectite clay, $TiO_2$, and lignosulfonate were identical in the clay-based gellants used in making emulsions 6 and 8, while the clay-based gellant used in making emulsion 5 had a relatively low $TiO_2$ content.

TABLE XII

| Emulsion # | Composition Parameters for the Key Ingredients | SPF | UVA/UVB Ratio |
|---|---|---|---|
| 1 | 6% Clay | 1.1 +/- 0.1 | 0.68 |
| 2 | 7.5% OMC | 8.9 +/- 1.2 | 0.21 |
| 3 | 7.5% OMC + 2% $TiO_2$ | 7.3 +/- 1.5 | 0.49 |
| 4 | 7.5% OMC + 2% $TiO_2$ + 3% Clay | 7.8 +/- 1.0 | 0.53 |
| 5 | 7.5% OMC + 0.6% $TiO_2$ + 5.88% Clay + 2.96% Lignosulfonate | 23.1 +/- 9.4 | 0.68 |
| 6 | 7.5% OMC + 2% $TiO_2$ + 3% Clay + 1.5% Lignosulfonate | 25.6 +/- 6.8 | 0.63 |
| 7 | 7.5% OMC +3% Avobenzone | 22.3 +/- 4.3 | |
| 8 | 7.5% OMC +3% Avobenzone + 2% $TiO_2$ + 3% Clay + 1.5% Lignosulfonate | 65.5 +/- 3.4 | |

As it appears from Table XII, both the organic sunscreen actives, OMC and avobenzone, seemed to be more effective in those sunscreen emulsions that contained lignosulfonate in combination with particulate materials such as a smectite clay and $TiO_2$. More significantly, such apparent enhancement of the UVR shielding functionality of an organic sunscreen in the presence of lignosulfonate-modified particulate materials seemed to be greater for the avobenzone system than for the OMC system. It may be recalled that no emulsifier was added in emulsion 8.

EXAMPLE 11

This example shows that, as an additive, a combination of a smectite clay, $TiO_2$, and lignosufonate can produce a much higher boost of SPF and UVA/UVB ratio in organic sunscreen-containing emulsions, than a combination of a smectite clay, $TiO_2$, and polyacrylate.

Sunscreen emulsions prepared with the composition parameters (based on the key ingredients) shown in Table XIII were SPF-tested as per the method described in EXAMPLE 6. The results of the SPF tests are given in Table XIII.

TABLE XIII

| Emulsion # | Composition Parameters for the Key Ingredients | SPF | UVA/UVB Ratio |
|---|---|---|---|
| 1 | 6.96% OMC (Control) | 9.3 +/- 0.8 | 0.24 |
| 2 | 6.96% OMC + 1.98% Clay + 1.98% $TiO_2$ + 0.65% Polyacrylate (SOKALAN PA 30 CL) | 16.0 +/- 2.0 | 0.45 |
| 3 | 6.96% OMC + 1.98% Clay + 1.98% $TiO_2$ + 0.65% Lignosulfonate (Vanisperse A) | 23.1 +/- 3.0 | 0.52 |

The method of preparation of the emulsions is described below. A stock emulsion containing 10.27% OMC by weight was prepared according to the formulation and procedure described in a section below. In a Waring blender was homogenized a mixture of 136.86 gram of the stock emulsion and given amounts of a smectite clay, $TiO_2$, dispersant (polyacrylate or lignosulfonate), water, electrolytes such as NaCl (added as a solid) and NaOH (added as a 15% w/w solution), and a defoamer. [Note that the particulate ingredients were added individually, together with a dispersant, rather than in the form of a mastergel.] The blender was operated at its maximum speed (22,000 rpm) for 3 minutes. The amount of electrolytes added correspond to about 0.39% of the total weight (201.9 gram) of the emulsion. The control emulsion (Emulsion 1) received all ingredients as in the test emulsions, excepting clay, $TiO_2$, and dispersant.

Stock Emulsion Formulation

| Sample | Phase | Ingredient | Function | % By Wt. |
|---|---|---|---|---|
| Stock | A | Deionized Water | Hydrophilic carrier | 35.62 |
| Emulsion | A | Propylene Glycol | Humectant | 3.42 |
| | A | Keltrol T (2%) | Thickener | 20.5 |
| | B | Lipomulse 165 | Emulsifier | 2.74 |
| | B | Octyl Methoxycinamate | Organic Sunscreen | 10.27 |
| | B | Lipowax D | Emulsifier | 5.48 |
| | B | Finsolv TN | Emollient | 13.7 |
| | B | DC 245 Fluid | Emollient | 5.0 |
| | C | Phenonip | Preservative | 1.37 |

Manufacturing Procedure:

Heat Phase A to 75° C.

Heat Phase B to 75° C.

Add Phase B to Phase A.

Cool to 45° C. and add Phase C.

Homogenize on Silverson homogenizer for 5 minutes @ 10,000 rpm.

EXAMPLE 12

This example shows that the SPF enhancement effect of the clay-based gellants disclosed herein could be achieved even for sunscreen emulsions that contain more than one organic sunscreen.

Sunscreen emulsions were prepared by homogenizing in a Waring blender (operated at 22,000 rpm for 3 minutes or until the emulsion appears uniform) a given portion of a stock emulsion (containing 7.5% OMC, w/w) such as the one described in EXAMPLE 11, with measured amounts of water and a second organic sunscreen such as octyl salicylate, with and without a clay-based gellant. These emulsions were SPF-tested by casting a film of the emulsion on a given area (with the application rate of 2 mg/cm$^2$) of Transpore tape (manufacturer: 3M Corporation) mounted on a glass slide, and then measuring the UV-absorbance of the film in the wavelength range of 290–400 nm. The results of the SPF tests are shown in Table XIV, along with the composition parameters for the key ingredients in the emulsions.

TABLE XIV

| Emulsion # | Composition Parameters for the Key Ingredients | SPF |
|---|---|---|
| 1 | 6.32% OMC + 4.5% Octyl salicylate | 13.3 |
| 2 | 6.32% OMC + 4.5% Octyl salicylate + 1.34% Clay + 1.34% TiO$_2$ + 0.27% Lignosulfonate (Vanisperse A) | 20.9 |

EXAMPLE 13

This example shows the SPF enhancement effect of a clay-based gellant of the present invention where the gellant is prepared by pre-dispersing TiO$_2$ in a lignosulfonate solution using a rotor-stator mixer (Ross-mixer), adding subsequently a smectite clay into the TiO$_2$ slurry under low-shear agitation, and finally passing the slurry of the clay-TiO$_2$ mixture once through a laboratory extruder (Hobart).

A clay-based gellant-containing emulsion was prepared by homogenizing in a Waring blender (operated at 22,000 rpm for 4 minutes) a stock emulsion such as the one described in EXAMPLE 11 with measured amounts of a clay-based gellant prepared as described above, and water (dosed with 0.026 g of sodium hydroxide). The emulsion was SPF-tested as per the method described in EXAMPLE 6, and the result is given in Table XV. To show the SPF enhancement effect of the clay-based gellant, Table XV includes the SPF of a control emulsion (Emulsion 1 in Table XIII, EXAMPLE 11) where the OMC content was only slightly lower than that in the test emulsion of the present example.

TABLE XV

| Emulsion # | Composition Parameters for the Key Ingredients | SPF | UVA/UVB Ratio |
|---|---|---|---|
| 1 | 6.96% OMC (Control) | 9.3 +/− 0.8 | 0.24 |
| 2 | 7% OMC + 2.95% Clay + 2.95% TiO$_2$ +0.59% Lignosulfonate (Vanisperse A from Borregaard LignoTech) | 31.3 +/− 5.2 | 0.55 |

EXAMPLE 14

This example shows a composition (Table XVI) and the SPF enhancement ability of clay-based gellants that do not contain any TiO$_2$.

TABLE XVI

| Wt. % of Clay | Wt. % of Dispersant | Wt. % Water |
|---|---|---|
| 17.05 | 27.3 | 53.84 |

The SPF of a sunscreen emulsion containing 7% OMC was found to be 12.5 as per the SPF testing method described in EXAMPLE 12. The addition of a smectite clay in combination with lignosulfonate (Vanisperse A) to such an emulsion composition (i.e., with 7% OMC) increased the SPF to 19.1. The amounts of clay and lignosulfonate in the emulsion correspond to 3% and 1.5%, respectively, based on the weight of the emulsion.

EXAMPLE 15

This example confirms that considerably stable emulsions can be made using the clay-based gellants disclosed herein, while not requiring the use of any emulsifying-surfactant.

An O/W emulsion was prepared by homogenizing a mixture of 36 g of light mineral oil, 65.96 g of deionized water, and 98.04 g of a clay-based gellant of the present invention, in a Waring blender. The forgoing mixture was homogenized for 10 minutes at 22,000 rpm, following which 0.5 g of a defoamer (Dow Corning 2210 antifoam), 0.1 g of TiO$_2$ and 15.4 g of propylene glycol was added to the resulting emulsion. Homogenization of the emulsion at 22,000 rpm was continued for an additional 5 minutes, following which it was degassed. The emulsion had a Brookfield viscosity of 11,250 cps at 10 rpm. It did not show any sign of syneresis after standing in an oven at 45° C. for about 45 days.

The clay-based gellant used in making the above emulsion has the following composition.

| No. | Ingredient | % By Weight |
|---|---|---|
| 1 | Clay-Polargel NF | 10.18 |
| 2 | TiO$_2$ | 0.2 |
| 3 | Dispersant (Ultrazine NAC, sodium lignosulfonate) | 20.3 |
| 4 | Sodium Chloride | 0.76 |
| 5 | Propylene Carbonate | 2.65 |
| 6 | Defoamer | 0.41 |
| 7 | Water | 65.5 |

EXAMPLE 16

This example shows that the clay-based gellants of the present invention could contain considerable amounts of water-immiscible (lipophilic) organic liquids (i.e., oils) as components. The emulsified oil-containing gellants are quite stable against separation of the oily components, inasmuch as no visual separation of oil could be seen even after 90 days of standing of an oil-containing mastergel sample.

In preparing the emulsified oil-containing mastergel (clay-based gellant) sample, a given amount of TiO2 was homogenized with given portions of two water-immiscible organic liquids (oils) in an aqueous solution of lignosulfonate and humate for 4.5 minutes. This was followed by the homogenization of a measured amount of a smectite clay in the emulsified oil-containing TiO$_2$ slurry for an additional 12 minutes. Homogenization was carried out using an industrial blender, wherein the TiO$_2$ and the oils were homogenized in the lignosulfonate-humate solution at 20,000 rpm. Homogenization of the clay in the TiO$_2$ slurry was carried out at a blender speed that corresponds to 16,000 rpm, while operating the blender at 40% of the maximum power-input. The mastergel composition, based on the key components, is given in Table XVII. The oils used are Finsolv TN (C$_{12-15}$ alkyl benzoate) and DowCorning 245 silicone fluid.

TABLE XVII

| Wt. % of Clay | Wt. % of TiO$_2$ | Wt. % of Ligno-sulfonate | Wt. % of Humate | Wt. % Finsolv TN | Wt. % of DC-245 Fluid | Wt. % of Water |
|---|---|---|---|---|---|---|
| 4.96 | 33.06 | 4.63 | 0.33 | 8.82 | 4.41 | 42.35 |

Many modifications and variations of the invention as hereinbefore set forth can be made without departing from the spirit and scope thereof, and, therefore, only such limitations should be imposed as are indicated by the appended claims.

What is claimed is:

1. A multifunctional additive composition for a cosmetic, a personal care, or a topical pharmaceutical formulation, comprising a particulate material, and a natural polymer other than carboxymethyl cellulose or xanthan gum, for addition to the formulation, said formulation including a hydrophilic liquid selected from the group consisting of water, a hydrophilic organic liquid, and mixtures thereof, said additive improving the efficacy of a sunscreen active material in said formulation, said sunscreen active capable of absorbing ultraviolet radiation in the UVA or UVB wavelength ranges, said additive performing at least one of the following functions when added to said cosmetic, personal care, or pharmaceutical formulation: (i) increasing the viscosity of a hydrophilic liquid selected from the group consisting of water, a hydrophilic organic liquid, and mixtures thereof; (ii) emulsifying and stabilizing oil droplets against creaming and coalescence in a hydrophilic liquid selected from the group consisting of water, a hydrophilic organic liquid, and mixtures thereof; and (iii) functioning as an antioxidant.

2. The additive composition of claim 1, wherein the sunscreen active material is selected from the group consisting of titanium dioxide, zinc oxide, octyl methoxycinamate, homosalate, octocrylene, octyl salicylate, methylbenzylidene camphor, phenylbenzylimaid-azole sulfonic acids, ethylhexyl triazone, oxybenzone, methyl anthranilate, avobenzone, and mixtures thereof.

3. The additive composition of claim 1, wherein the additive is in a form selected from the group consisting of a slurry of the particulate material in a hydrophilic liquid that contains the natural polymer in solution; and an admixture of the particulate material and the natural polymer.

4. The additive composition of claim 3, wherein the particulate material is selected from the group consisting of a smectite clay, an inorganic oxide, colloidal silica, laponite, alumina, oil droplets, a pigment, a latex polymer, and mixtures thereof.

5. The additive composition of claim 4, wherein the smectite clay is selected from the group consisting of bentonite, montmorillonite, saponite, hectorite, bidelite, stevensite, and mixtures thereof.

6. The additive composition of claim 4, wherein the particulate material comprises an inorganic metal oxide-based sunscreen active compound selected from the group consisting of TiO$_2$, ZnO, and mixtures thereof.

7. The additive composition of claim 4, wherein the particulate material comprises oil droplets selected from the group consisting of vegetable oil, flower oil, mineral oil, silicone oil, petroleum-derived oil, a hydrocarbon and mixtures thereof.

8. The additive composition of claim 4, wherein the particulate material is selected from the group consisting of a smectite clay, an inorganic oxide, and mixtures thereof.

9. The additive composition of claim 8, wherein the particulate material comprises 0 to 100% smectite clay and with the balance of the particulate material being an inorganic oxide or a mixture of inorganic oxides.

10. The additive composition of claim 9, wherein the particulate material comprises 1% to 100% smectite clay and with the balance of the particulate material being an inorganic oxide or a mixture of inorganic oxides.

11. The additive composition of claim 10. wherein the particulate material comprises 10% to 90% smectite clay and with the balance of the particulate material being an inorganic oxide or a mixture of inorganic oxides.

12. The additive composition of claim 8, wherein the particulate material comprises a smectite clay selected from the group consisting of bentonite, montmorillonite, saponite, hectorite, bidelite, stevensite, and mixtures thereof.

13. The additive composition of claim 8, wherein the particulate material comprises an inorganic metal oxide-based sunscreen active compound selected from the group consisting of TiO$_2$, ZnO, and mixtures thereof.

14. The additive composition of claim 3, wherein the natural polymer is a polyphenolic polymer selected from the group consisting of a lignosulfonate, lignin, humate, tannate, their derivatives, and mixtures thereof.

15. The additive composition of claim 14, wherein the polyphenolic, natural polymer is selected from the group consisting of a lignosulfonate; kraft lignin; sulfonated kraft lignin; oxylignin; sulfonated oxylignin; humate; sulfonated humate; tannate; sulfonated tannate; lignosulfonate copolymerized with a monomer selected from the group consisting of acrylate, acrylic acid, acrylamide, styrene sulfonate, and naphthalene sulfonate; azoligno-sulfonate; azolignin; lignosulfonate-formaldehyde condensates; lignin-formaldehyde condensates; humate-formaldehyde condensates; tannate-formaldehyde condensates; hydrophobically-modified lignosulfonate; hydrophobically-modified lignin; hydrophobically-modified humate; hydrophobically-modified tannate; cationically-modified lignosulfonate; cationically-modified lignin; cationically-modified humate; cationically-modified tannate; amino lignosulfonate; amino lignin; amino humate; alkylated lignosulfonate; alkylated lignin; alkylated humate; crosslinked lignosulfonate; crosslinked lignin; and mixtures thereof.

16. The additive composition of claim 3, wherein the additive is in slurry form, and the hydrophilic liquid is water or a mixture of water and a hydrophilic organic liquid selected from the group consisting of glycerol, propylene glycol, isopropanol, ethanol, polyethylene glycol, and mixtures thereof.

17. The additive composition of claim 3, wherein the particulate material is included in an amount of about 1% to about 95% by weight, based on the total weight of the additive composition.

18. The additive composition of claim 17, wherein the particulate material(s) is included in an amount of about 10% to about 65% by weight, based on the total weight of the additive composition.

19. The additive composition of claim 3, wherein the natural polymer is included in an amount of about 0.05% to about 300% based on the weight of particulate material in the additive composition.

20. The additive composition of claim 19, wherein the natural polymer is included in an amount of about 5% to about 100% based on the weight of particulate material in the additive composition.

21. The additive composition of claim 20, wherein the natural polymer is included in an amount of about 10% to about 60% based on the weight of particulate material in the additive composition.

22. The additive composition of claim 3, further including a protein selected from the group consisting of gelatin, soy protein, wheat protein, casein, and mixtures thereof.

23. The additive composition of claim 22, containing about 0.1–5% of a protein gellant.

24. The additive composition of claim 23, wherein the protein gellant is gelatin.

25. The additive composition of claim 3, further containing about 0.1–5% of a gellant selected from the group consisting of xanthan gum, polyacrylate, hydrophobically-modified polyacrylate, and mixtures thereof.

26. The additive composition of claim 3, wherein the particulate material comprises emulsified oil droplets, and wherein the natural polymer emulsifies and stabilizes the emulsified oil droplets against flocculation and coalescence.

27. The additive composition of claim 3, wherein the natural polymer is an antioxidant containing a polyphenol functionality.

28. A method of enhancing the efficacy of a sunscreen composition containing an ultraviolet radiation filter material selected from the group consisting of titanium dioxide, zinc oxide, octyl methoxycinamate, homosalate, octocrylene, octyl salicylate, methylbenzylidene camphor, phenylbenzyimaidazole sulfonic acid, ethlhexyl triazone, oxybenzone, methyl anthranilate, avobenzone, and mixtures thereof, comprising adding to said sunscreen composition the additive composition of claim 1.

29. A method of enhancing the efficacy of a sunscreen composition containing a hydrophilic liquid selected from the group consisting of water or a mixture of water and a hydrophilic organic liquid selected from the group consisting of glycerol, propylene glycol, isopropanol, ethanol, polyethylene glycol, and mixtures thereof, and an ultraviolet radiation filter material selected from the group consisting of titanium dioxide, zinc oxide, octyl methoxycinamate, homosalate, octocrylene, octyl salicylate, methylbenzylidene camphor, phenylbenzyimaidazole sulfonic acids, ethihexyl triazone, oxybenzone, methyl anthranilate, avobenzone, and mixtures thereof, comprising adding to said sunscreen composition the additive composition of claim 3.

30. A composition selected from the group consisting of cosmetic, personal care, and topical pharmaceutical formulations, obtained after incorporating into the formulation the multifunctional additive composition of claim 1, wherein the cosmetic, personal care or topical pharmaceutical formulation includes one or more particulate materials, one or more natural polymers, and a hydrophilic liquid selected from the group consisting of water, a hydrophilic organic liquid, and mixtures thereof.

31. The composition of claim 30, wherein the particulate material is selected from the group consisting of a smectite clay, an inorganic oxide, colloidal silica, laponite, alumina, an oil, a pigment, a latex polymer, an emollient as oil droplets, and mixtures thereof.

32. The composition of claim 31, wherein the particulate material comprises a smectite clay selected from the group consisting of bentonite, montmorillonite, saponite, hectorite, bidelite, stevensite, and mixtures thereof.

33. The composition of claim 31, wherein the particulate material comprises an inorganic metal oxide-based sunscreen active compound selected from the group consisting of $TiO_2$, $ZnO$, and mixtures thereof.

34. The composition of claim 31, wherein the particulate material comprises oil droplets selected from the group consisting of vegetable oil, flower oil, mineral oil, silicone oil, petroleum-derived oil, a hydrocarbon, an organic sunscreen compound, and mixtures thereof.

35. The composition of claim 31, wherein the particulate material is selected from the group consisting of a smectite clay, an inorganic oxide, and mixtures thereof.

36. The composition of claim 35, wherein the particulate material comprises 0 to 100% smectite clay and with the balance of the particulate material being an inorganic oxide or a mixture of inorganic oxides.

37. The composition of claim 36, wherein the particulate material comprises 1% to 100% smectite clay and with the balance of the particulate material being an inorganic oxide or a mixture of inorganic oxides.

38. The composition of claim 37, wherein the particulate material comprises 1% to 99% smectite clay and with the balance of the particulate material being an inorganic oxide or a mixture of inorganic oxides.

39. The composition of claim 38, wherein the particulate material comprises 10% to 90% smectite clay and with the balance of the particular material being an inorganic oxide or a mixture or inorganic oxides.

40. The composition of claim 35, wherein the particulate material is a smectite clay selected from the group consisting of bentonite, montmorillonite, saponite, hectorite, bidelite, stevensite, and mixtures thereof.

41. The composition of claim 35, wherein the particulate material is an inorganic metal oxide-based sunscreen active compound selected from the group consisting of $TiO_2$, $ZnO$, and mixtures thereof.

42. The composition of claim 30, wherein the natural polymer is a polyphenolic polymer selected from the group consisting of a lignosulfonate, lignin, humate, tannate, their derivatives, and mixtures thereof.

43. The composition of claim 42, wherein the polyphenolic, natural polymer is selected from the group consisting of lignosulfonate; kraft lignin; sulfonated kraft lignin; oxylignin; sulfonated oxylignin; humate; sulfonated humate; tannate; sulfonated tannate; lignosulfonate copolymerized with a monomer selected from the group consisting of acrylate, acrylic acid, acrylamide, styrene sulfonate, and naphthalene sulfonate; azoligno-sulfonate; azolignin; lignosulfonate-formaldehyde condensates; lignin-formaldehyde condensates; humate-formaldehyde condensates; tannate-formaldehyde condensates; hydrophobically-modified lignosulfonate; hydrophobically-modified lignin; hydrophobically-modified humate; hydrophobically-modified tannate; cationically-modified lignosulfonate; cationically-modified lignin; cationically-modified humate; cationically-modified tannate; amino lignosulfonate; amino lignin; amino humate; alkylated lignosulfonate; alkylated lignin; alkylated humate; crosslinked lignosulfonate; crosslinked lignin; and mixtures thereof.

44. The composition of claim 30, wherein the hydrophilic organic liquid is selected from the group consisting of glycerol, propylene glycol, isopropanol, ethanol, polyethylene glycol, and mixtures thereof.

45. The composition of claim 30, wherein the particulate material is included in the composition in an amount of about 0.05% to about 30% by weight, based on the total weight of the composition.

46. The composition of claim 45, wherein the particulate material is included in the composition in an amount of about 0.1% to about 15% by weight, based on the total weight of the composition.

47. The composition of claim 30, wherein the natural polymer is included in the composition in an amount of about 0.05% to about 300% based on the weight of particulate material in the composition.

48. The composition of claim 47, wherein the natural polymer is included in the composition in an amount of about 5% to about 100% based on the weight of particulate material in the composition.

49. The composition of claim 48, wherein the natural polymer is included in the composition in an amount of about 10% to about 60% based on the weight of particulate material in the composition.

50. The composition of claim 30, further including a protein selected from the group consisting of gelatin, soy protein, wheat protein, casein, and mixtures thereof.

51. The composition of claim 50, containing about 0.1–1% of a protein gellant.

52. The composition of claim 51, wherein the protein gellant is gelatin.

53. The composition of claim 30, further containing about 0.1–1% of a gellant selected from the group consisting of xanthan gum, polyacrylate, hydrophobically-modified polyacrylate, and mixtures thereof.

54. The composition of claim 30, wherein the composition includes emulsified oil droplets, and the natural polymer emulsifies and stabilizes the emulsified oil droplets against flocculation and coalescence.

55. The composition of claim 30, wherein the natural polymer is an antioxidant containing a polyphenol functionality.

56. A method of manufacturing an additive composition for a cosmetic or a personal care or a pharmaceutical formulation, comprising dispersing a particulate material selected from the group consisting of solid particles, oil droplets, and mixtures thereof, in a hydrophilic liquid selected from the group consisting of water, a hydrophilic organic liquid, and mixtures thereof, wherein the hydrophilic liquid contains a dissolved, natural polymer other than carboxymethyl cellulose or xanthan gum.

57. The method of claim 56, wherein the particulate material is selected from the group consisting of a smectite clay, an inorganic oxide, colloidal silica, laponite, alumina, a pigment, oil droplets, a latex polymer, and mixtures thereof.

58. The method of claim 57, wherein the smectite clay is selected from the group consisting of bentonite, montmorillonite, saponite, hectorite, bidelite, stevensite, and mixtures thereof.

59. The method of claim 57, wherein the particulate material comprises an inorganic metal oxide-based sunscreen active compound selected from the group consisting of $TiO_2$, ZnO, and mixtures thereof.

60. The method of claim 57, wherein the particulate material comprises oil droplets selected from the group consisting of vegetable oil, flower oil, mineral oil, silicone oil, petroleum-derived oil, a hydrocarbon liquid, and mixtures thereof.

61. The method of claim 57, wherein the particulate material is selected from the group consisting of a smectite clay, an inorganic oxide, and mixtures thereof.

62. The method of claim 61, wherein the particulate material comprises 0 to 100% smectite clay and with the balance of the particulate material being an inorganic oxide or mixtures of inorganic oxides.

63. The method of claim 62, wherein the particulate material comprises 1% to 100% smectite clay and with the balance of the particulate material being an inorganic oxide or mixtures of inorganic oxides.

64. The method of claim 63, wherein the particulate material comprises 1% to 99% smectite clay and with the balance of the particulate material being an inorganic oxide or a mixture of inorganic oxides.

65. The method of claim 64, wherein the particulate material comprises 10% to 90% smectite clay and with the balance of the particulate material being an inorganic oxide or a mixture of inorganic oxides.

66. The method of claim 61, wherein the particulate material comprises a smectite clay selected from the group consisting of bentonite, montmorillonite, saponite, hectorite, bidelite, stevensite, and mixtures thereof.

67. The method of claim 61, wherein the particulate material comprises an inorganic metal oxide-based sunscreen active compound selected from the group consisting of $TiO_2$, ZnO, and mixtures thereof.

68. The method of claim 56, wherein the natural polymer is a polyphenolic polymer selected from the group consisting of a lignosulfonate, lignin, humate, tannate, a derivative thereof, and mixtures thereof.

69. The method of claim 68, wherein the polyphenolic, natural polymer is selected from the group consisting of lignosulfonate; kraft lignin; sulfonated kraft lignin; oxylignin; sulfonated oxylignin; humate; sulfonated humate; tannate; sulfonated tannate; lignosulfonate copolymerized with a monomer selected from the group consisting of acrylate, acrylic acid, acrylamide, styrene sulfonate, and naphthalene sulfonate; azoligno-sulfonate; azolignin; lignosulfonate-formaldehyde condensates; lignin-formaldehyde condensates; humate-formaldehyde condensates; tannate-formaldehyde condensates; hydrophobically-modified lignosulfonate; hydrophobically-modified lignin; hydrophobically-modified humate; hydrophobically-modified tannate; cationically-modified lignosulfonate; cationically-modified lignin; cationically-modified humate; cationically-modified tannate; amino lignosulfonate; amino lignin; amino humate; alkylated lignosulfonate; alkylated lignin; alkylated humate; crosslinked lignosulfonate; crosslinked lignin; and mixtures thereof.

70. The method of claim 56, wherein the hydrophilic organic liquid is selected from the group consisting of glycerol, propylene glycol, isopropanol, ethanol, polyethylene glycol, and mixtures thereof.

71. The method of claim 56, wherein the particulate material is included in the additive composition in an amount of about 1% to about 65% by weight, based on the total weight of the composition.

72. The method of claim 71, wherein the particulate material is included in the additive composition in an amount of about 10% to about 65% by weight, based on the total weight of the composition.

73. The method of claim 56, wherein the natural polymer is included in the additive composition in an amount of about 0.05% to about 300% based on the weight of particulate material in the composition.

74. The method of claim 73, wherein the natural polymer is included in the additive composition in an amount of about 5% to about 100% based on the weight of particulate material in the composition.

75. The method of claim 74, wherein the natural polymer is included in the additive composition in an amount of about 10% to about 60% based on the weight of particulate material in the composition.

76. The method of claim 56, wherein the additive composition further includes a protein selected from the group consisting of gelatin, soy protein, wheat protein, casein, and mixtures thereof.

77. The method of claim 76, wherein the additive composition contains about 0.1–5% of a protein gellant.

78. The method of claim 77, wherein the protein gellant is gelatin.

79. The method of claim 56, wherein the additive composition further contains about 0.1–5% of a gellant selected from the group consisting of xanthan gum, polyacrylate, hydrophobically-modified polyacrylate, and mixtures thereof.

80. The method of claim 56, wherein the additive composition includes emulsified oil droplets, and wherein the natural polymer emulsifies and stabilizes the emulsified oil droplets against flocculation and coalescence.

81. The method of claim 56, wherein the natural polymer is an antioxidant containing a polyphenol functionality.

82. The method of claim 56, wherein the natural polymer is dissolved in the hydrophilic liquid to form a solution of said natural polymer, prior to adding the particulate material thereto.

83. The method of claim 82, wherein the natural polymer solution and the particulate material are mixed with sufficient energy to homogeneously disperse the particulate material in the natural polymer-containing hydrophilic liquid.

84. A mastergel composition comprising about 1–65% by weight of a particulate material selected from the group consisting of a smectite clay, an inorganic oxide, and mixtures thereof, and about 0.05–60% by weight of a polyphenolic, natural polymer selected from the group consisting of a lignosulfonate, lignin, humate, tannate, a derivative thereof, and mixtures thereof.

85. The composition of claim 84, wherein the polyphenolic, natural polymer is selected from the group consisting of lignosulfonate; kraft lignin; sulfonated kraft lignin; oxylignin; sulfonated oxylignin; humate; sulfonated humate; tannate; sulfonated tannate; lignosulfonate copolymerized with a monomer selected from the group consisting of acrylate, acrylic acid, acrylamide, styrene sulfonate, and naphthalene sulfonate; azoligno-sulfonate; azolignin; lignosulfonate-formaldehyde condensates; lignin-formaldehyde condensates; humate-formaldehyde condensates; tannate-formaldehyde condensates; hydrophobically-modified lignosulfonate; hydrophobically-modified lignin; hydrophobically-modified humate; hydrophobically-modified tannate; cationically-modified lignosulfonate; cationically-modified lignin; cationically-modified humate; cationically-modified tannate; amino lignosulfonate; amino lignin; amino humate; alkylated lignosulfonate; alkylated lignin; alkylated humate; crosslinked lignosulfonate; crosslinked lignin; and mixtures thereof.

86. The composition of claim 84, wherein the particulate material comprises a smectite clay selected from the group consisting of bentonite, montmorillonite, saponite, hectorite, bidelite, stevensite, and mixtures thereof.

87. The composition of claim 84, wherein the particulate material comprises a metal oxide-based sunscreen active compound selected from the group consisting of $TiO_2$, ZnO, and mixtures thereof.

88. The composition of claim 84, wherein the particulate material comprises a smectite clay material that is at least partially exfoliated.

89. A method of manufacturing a stable, homogeneous gel for use as an additive in a cosmetic or a personal care, or a pharmaceutical formulation, having dispersed particulate material that is stable against coagulation, comprising the steps of:
  a) dissolving a natural polymer in a hydrophilic liquid selected from the group consisting of water, a hydrophilic organic liquid, and mixtures thereof to form a solution of the natural polymer;
  b) adding a particulate material comprising a smectite clay to said natural-polymer solution, with sufficient mixing to homogeneously disperse the particulate material in the natural-polymer solution; and
  c) shearing the material from step (b) sufficiently to achieve exfoliation of at least a portion of the dispersed smectite clay to form a stable gel containing individual clay platelets, wherein said natural polymer is adsorbed on the surface of the clay platelets, to form said stable gel; wherein the natural polymer is included in the gel in an amount of about 0.05% to about 300% by weight, based on the total weight of said particulate material in the gel.

90. The method of claim 89, further including adding an inorganic oxide to the natural polymer solution, and wherein the smectite clay and inorganic oxide are added during agitation of the solution of the natural polymer to form a mixture, followed by shearing the mixture for a time sufficient to form a gel.

91. The method of claim 89, wherein the particulate material contains between 0% and 100% smectite clay and with the balance of the particulate material being an inorganic oxide or a mixture of inorganic oxides.

92. The method of claim 91, wherein the particulate material comprises 1% to 99% smectite clay and with the balance of the particulate material being an inorganic oxide or a mixture of inorganic oxides.

93. The method of claim 92, wherein the particulate material comprises 10% to 90% smectite clay and with the balance of the particulate material being an inorganic oxide or a mixture of inorganic oxides.

94. The method of claim 89, wherein the hydrophilic liquid comprises water or a mixture of water and a hydrophilic organic liquid selected from the group consisting of glycerol, propylene glycol, isopropanol, ethanol, polyethylene glycol, and mixtures thereof, wherein the concentration of water is greater than the concentration of hydrophilic organic liquid.

95. The method of claim 89, wherein the smectite clay is selected from the group consisting of bentonite, montmorillonite, saponite, hectorite, bidelite, stevensite, and mixtures thereof.

96. The method of claim 89, wherein the inorganic oxide particulate material comprises a metal oxide-based sunscreen active compound selected from the group consisting of $TiO_2$, ZnO, and mixtures thereof.

97. The method of claim 89, wherein the natural polymer is a polyphenolic polymer selected from the group consisting of a lignosulfonate, lignin, humate, tannate, a derivative thereof, and mixtures thereof.

98. The method of claim 97, wherein the natural polymer is a polyphenolic polymer selected from the group consisting of a lignosulfonate; kraft lignin; sulfonated kraft lignin; oxylignin; sulfonated oxylignin; humate; sulfonated humate; tannate; sulfonated tannate; lignosulfonate copolymerized with a monomer selected from the group consisting of acrylate, acrylic acid, acrylamide, styrene sulfonate, and naphthalene sulfonate; azoligno-sulfonate; azolignin; lignosulfonate-formaldehyde condensates; lignin-formaldehyde condensates; humate-formaldehyde condensates; tannate-formaldehyde condensates; hydrophobically-modified lignosulfonate; hydrophobically-modified lignin; hydrophobically-modified humate; hydrophobically-modified tannate; cationically-modified lignosulfonate; cationically-modified lignin; cationically-modified humate; cationically-modified tannate; amino lignosulfonate; amino lignin; amino humate; alkylated lignosulfonate; alkylated lignin; alkylated humate; crosslinked lignosulfonate; crosslinked lignin; and mixtures thereof.

99. The method of claim 89, wherein the weight average molecular weight of the natural polymer is in the range of about 5,000 to about 100,000.

100. The method of claim 89, further including the step of diluting the gel with additional hydrophilic organic liquid such that the weight ratio of hydrophilic organic liquid to water is in the range of about 1:1 to about 6:1.

101. The method of claim 89, wherein the natural polymer is not a gum or a starch.

102. The method of claim 89, wherein the particulate material has a particle size such that at least 90% of the particles have a particle size less than or equal to about 30 micron.

103. A method of manufacturing a cosmetic or a personal care or a pharmaceutical composition comprising dissolving one or more natural polymers in a hydrophilic liquid to form a natural polymer solution, and dispersing a particulate material in the natural polymer solution, said particulate material selected from the group consisting of a solid particulate material, a lipophilic organic liquid or an oil, and mixtures thereof, wherein the hydrophilic liquid is selected from the group consisting of water, a hydrophilic organic liquid, and mixtures thereof.

104. The method of claim 103, wherein the particulate material is selected from the group consisting of a smectite clay, an inorganic oxide, colloidal silica, laponite, alumina, oil droplets, pigments, a latex polymer, and mixtures thereof.

105. The method of claim 104, wherein the particulate material comprises a smectite clay selected from the group consisting of bentonite, montmorillonite, saponite, hectorite, bidelite, stevensite, and mixtures thereof.

106. The method of claim 104, wherein the particulate material comprises an inorganic metal oxide-based sunscreen active compound selected from the group consisting of $TiO_2$, ZnO, and mixtures thereof.

107. The method of claim 104, wherein the particulate material comprises oil droplets selected from the group consisting of vegetable oil, flower oil, mineral oil, silicone oil, petroleum-derived oil, organic sunscreen, hydrocarbon oil, and mixtures thereof.

108. The method of claim 104, wherein the particulate material is selected from the group consisting of a smectite clay, an inorganic oxide, and mixtures thereof.

109. The method of claim 108, wherein the particulate material comprises 0 to 100% smectite clay and with the balance of the particulate material being an inorganic oxide or mixtures of inorganic oxides.

110. The method of claim 109, wherein the particulate material comprises 1% to 99% smectite clay and with the balance of the particulate material being the inorganic oxide or a mixture of inorganic oxides.

111. The method of claim 110 wherein the particulate mixture comprises 10% to 90% smectite clay and with the balance of the particulate material being the inorganic oxide or a mixture of inorganic oxides.

112. The method of claim 108, wherein the particulate material comprises a smectite clay selected from the group consisting of bentonite, montmorillonite, saponite, hectorite, bidelite, stevensite, and mixtures thereof.

113. The method of claim 106, wherein the particulate material comprises an inorganic metal oxide-based sunscreen active compound selected from the group consisting of $TiO_2$, ZnO, and mixtures thereof.

114. The method of claim 103, herein the natural polymer is a polyphenolic polymer selected from the group consisting of lignosulfonates, lignin, humates, tannates, their derivatives, and mixtures thereof.

115. The method of claim 114, wherein the natural polymer is a polyphenolic polymer selected from the group consisting of a lignosulfonate; kraft lignin; sulfonated kraft lignin; oxylignin; sulfonated oxylignin; humate; sulfonated humate; tannate; sulfonated tannate; lignosulfonate copolymerized with a monomer selected from the group consisting of acrylate, acrylic acid, acrylamide, styrene sulfonate, and naphthalene sulfonate; azoligno-sulfonate; azolignin; lignosulfonate-formaldehyde condensates; lignin-formaldehyde condensates; humate-formaldehyde condensates; tannate-formaldehyde condensates; hydrophobically-modified lignosulfonate; hydrophobically-modified lignin; hydrophobically-modified humate; hydrophobically-modified tannate; cationically-modified lignosulfonate; cationically-modified lignin; cationically-modified humate; cationically-modified tannate; amino lignosulfonate; amino lignin; amino humate; alkylated lignosulfonate; alkylated lignin; alkylated humate; crosslinked lignosulfonate; crosslinked lignin; and mixtures thereof.

116. The method of claim 103, wherein the hydrophilic organic liquid is selected from the group consisting of glycerol, propylene glycol, isopropanol, ethanol, polyethylene glycol, and mixtures thereof.

117. The method of claim 103, wherein the particulate material is included in the composition in an amount of about 0.05% to about 30% by weight, based on the total weight of the composition.

118. The method of claim 117, wherein the particulate material is included in the composition in an amount of about 0.1% to about 15% by weight, based on the total weight of the composition.

119. The method of claim 103, wherein the natural polymer is included in the composition in an amount of about 0.05% to about 300% based on the weight of particulate material in the composition.

120. The method of claim 119, wherein the natural polymer is included in the composition in an amount of about 5% to about 100% based on the weight of particulate material in the composition.

121. The composition of claim 120, wherein the natural polymer is included in the composition in an amount of about 10% to about 60% based on the weight of particulate material in the composition.

122. The method of claim 103, wherein the composition further includes a protein selected from the group consisting of gelatin, soy protein, wheat protein, casein, and mixtures thereof.

123. The method of claim 103, wherein the composition contains about 0.1–1% of a protein gellant.

124. The method of claim 123, wherein the protein gellant is gelatin.

125. The method of claim 103, wherein the composition further contains about 0.1–1% of a gellant selected from the group consisting of xanthan gum, polyacrylate, hydrophobically-modified polyacrylate, and mixtures thereof.

126. The method of claim 103, wherein the particulate material comprises emulsified oil droplets, and the natural polymer emulsifies and stabilizes the emulsified oil droplets in the composition, against flocculation and coalescence.

127. The method of claim 103, wherein the natural polymer is an antioxidant containing a polyphenol functionality.

128. A method of enhancing a property of skin or hair, said property selected from the group consisting of feel, appearance, ultraviolet radiation protection, and combinations thereof, comprising applying to said skin or hair the additive composition of claim 1.

129. A cosmetic or personal care or pharmaceutical composition containing the multifunctional additive composition of claim 1 to form a final composition, wherein the final composition is in a form selected from the group consisting of an oil-in-water emulsion; a water-in-oil emulsion; and an aqueous gel.

130. A cosmetic or personal care or pharmaceutical composition containing the multifunctional additive composition of claim 1, wherein said composition is selected from the group consisting of a skin-care cream, a skin-care lotion, a sunscreen formulation, a shampoo, a hair conditioner, a hair colorant, a hair styling aid, a liquid makeup, a foundation, a shaving cream, a shaving cream lotion, a topical drug, an antiperspirant, and mixtures thereof.

131. The cosmetic or personal care or pharmaceutical composition of claim 130 containing the multifunctional additive composition of claim 1 to form a final composition, wherein the composition of claim 1 is included in the final composition in an amount ranting from 0.1 to 35% by weight, based on the total weight of the final composition.

132. The cosmetic or personal care or pharmaceutical composition of claim 131, wherein the composition is manufactured without adding an emulsifying surfactant, to provide a composition that is not irritating to skin.

133. A method of increasing the viscosity of a cosmetic or personal care or pharmaceutical composition containing a hydrophilic solvent comprising adding to said composition the multifunctional additive composition of claim 1.

134. The method of claim 133, wherein the hydrophilic solvent is selected from the group consisting of water, a glycol, glycerol, alcohol, and mixtures thereof, and the hydrophilic solvent is contained in the cosmetic composition in an amount of about 1% to about 95% by weight, based on the total weight of the final composition.

135. The method of claim 134, wherein the hydrophilic solvent comprises about 5% to about 80% by weight of the final composition.

* * * * *

UNITED STATES PATENT AND TRADEMARK OFFICE
CERTIFICATE OF CORRECTION

PATENT NO.    : 6,500,411 B2
DATED         : December 31, 2002
INVENTOR(S)   : Ashoke K. SenGupta et al.

It is certified that error appears in the above-identified patent and that said Letters Patent is hereby corrected as shown below:

<u>Column 28,</u>
Line 11, please change "ethihexyl triazone" to -- ethlhexyl triazone --.

<u>Column 34,</u>
Line 37, please change "claim 103, herein" to -- claim 103, wherein --.

Signed and Sealed this

Sixteenth Day of September, 2003

JAMES E. ROGAN
*Director of the United States Patent and Trademark Office*